US009434962B2

(12) United States Patent
Koskinen et al.

(10) Patent No.: US 9,434,962 B2
(45) Date of Patent: *Sep. 6, 2016

(54) INTEGRATED PROCESS FOR PRODUCING BIOFUELS

(75) Inventors: Perttu Koskinen, Helsinki (FI); Reijo Tanner, Hikia (FI)

(73) Assignee: Neste Oyj, Espoo (FI)

( * ) Notice: Subject to any disclaimer, the term of this patent is extended or adjusted under 35 U.S.C. 154(b) by 786 days.

This patent is subject to a terminal disclaimer.

(21) Appl. No.: 13/333,195

(22) Filed: Dec. 21, 2011

(65) Prior Publication Data

US 2012/0159839 A1    Jun. 28, 2012

Related U.S. Application Data

(60) Provisional application No. 61/459,963, filed on Dec. 22, 2010.

(30) Foreign Application Priority Data

Dec. 22, 2010  (EP) .................................. 10196556

(51) Int. Cl.
| | | |
|---|---|---|
| *C12P 7/64* | (2006.01) | |
| *C12P 7/16* | (2006.01) | |
| *C12N 9/42* | (2006.01) | |
| *C12N 9/24* | (2006.01) | |
| *C12P 7/10* | (2006.01) | |

(52) U.S. Cl.
CPC ................. *C12P 7/16* (2013.01); *C12N 9/248* (2013.01); *C12N 9/2437* (2013.01); *C12P 7/10* (2013.01); *C12P 7/6463* (2013.01); *Y02E 50/10* (2013.01); *Y02E 50/13* (2013.01); *Y02E 50/16* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| 7,691,792 B1 | 4/2010 | Fisher et al. | |
|---|---|---|---|
| 2007/0161095 A1 | 7/2007 | Gurin | |
| 2009/0011480 A1 | 1/2009 | Trimbur et al. | |
| 2009/0064567 A1* | 3/2009 | Lippmeier et al. | 44/308 |
| 2009/0181440 A1 | 7/2009 | Rush | |
| 2009/0217569 A1 | 9/2009 | Pastinen et al. | |
| 2010/0028484 A1 | 2/2010 | Kriesler et al. | |
| 2010/0151538 A1* | 6/2010 | Franklin et al. | 435/134 |
| 2010/0297749 A1* | 11/2010 | Aravanis et al. | 435/289.1 |
| 2011/0027827 A1* | 2/2011 | Chi et al. | 435/41 |

FOREIGN PATENT DOCUMENTS

| CN | 101148630 | 3/2008 |
|---|---|---|
| EP | 1396531 | 3/2004 |
| EP | 1398364 | 3/2004 |
| EP | 1741767 | 1/2007 |
| EP | 1741768 | 1/2007 |
| WO | 2009035551 | 3/2009 |
| WO | 2009098365 | 8/2009 |
| WO | 2010006228 | 1/2010 |
| WO | 2010042819 | 4/2010 |
| WO | 2010042842 | 4/2010 |
| WO | 2010046051 | 4/2010 |
| WO | 2010060056 | 5/2010 |
| WO | 2011103428 | 8/2011 |

OTHER PUBLICATIONS

Sukumaran et al., J. Sci. Ind. Res., 64:832-844 (2005).*
Meng et al., Renew. Energy, 34:1-5 (2009).*
Peng et al., Biores. Tech., 99:3885-3889 (2008).*
Fukuda et al., Biochem. Eng. J., 44:2-12 (2009).*
Himmel et al., Science, 315:804-807 (2007).*
Tengerdy et al., Biochem. Eng. J., 13:169-179 (2003).*
Verdoes et al., App. Microbiol. Biotechnol., 43:195-205 (1995).*
Hamelinck et al., Energy Policy, 34:3268-3283 (2006).*
Meher et al., Renew. Sust. Energy Rev., 10:248-268 (2006).*
Appukuttan et al., J. Agric. Food Chem., 56:3981-3988 (2008).*
Fang et al., J. Mol. Cata. B: Enz., 49:36-42 (2007).*
Kavya et al., Pol. J. Microbiol., 58(2):125-130 (2009).*
Singh et al., Let. App. Microbiol., 12:200-202 (1991).*
Kamat et al., Biores. Technol., 135:246-253 (2013).*
Baer et al., "Effect of butanol challenge and temperatuve on lipid composition and membrane fluidity of butanol-tolerant Clostridium acetobutylicum", Applied and Environmental Microbiology, Dec. 1987, 53(12):2854-2861.
Fall et al., "Bioconversion of Xylan to triglycerides by oil-rich yeasts", Applied and Environmental Microbiology, May 1984, 47(5):1130-1134.

(Continued)

*Primary Examiner* — Thomas J Visone
(74) *Attorney, Agent, or Firm* — Andrus Intellectual Property Law, LLP

(57) ABSTRACT

Disclosed is an integrated process comprising first and second biotechnical processes. The first process produces biofuel and/or starting material for biofuel and uses a microorganism capable of producing enzymes. The second process produces biofuel and/or starting material for biofuel. In the integrated process, the microorganisms are cultivated and biofuel and/or starting material for biofuel and enzymes are produced. The microorganism culture, supernatant or a protein enriched fraction or a dilution of the supernatant comprising catalytically active enzyme(s) are introduced into the first and/or into the second process, or feedstock for the process(es) is treated. The invention relates also to use of the produced enzymes in biofuel production process or in other applications as an enzyme preparation or a source of enzymes. The invention relates also to use of the produced lipids and alcohols as biofuel, a component of biofuel or a starting material for biofuel production.

13 Claims, 12 Drawing Sheets

(56) References Cited

OTHER PUBLICATIONS

Hui et al., "Direct microbial conversion of wheat straw into lipid by a cellulolytic fungus of Aspergillus oryzae A-4 in solid-state fermentation", Bioresource Technology, 2010, 101:7556-7562.

Ismail et al., "Production of hemicellulytic enzymes by fungi", Agricultural Wastes, 1986, 18:283-288.

Lynd et al., "Consolidated bioprocessing of cellulosic biomass: an update", Current Opinion in Biotechnology, 2005, 16:577-583.

Peng et al., "Microbial oil accumulation and cellulase secretion of the endophytic fungi from oleaginous plants", Annals of Microbiology, 2007, 57(2):239-242.

Suutari et al., "Temperature adaptation in yeasts: the role of fatty acids", Journal of General Microbiology, 1990, 136:1469-1474.

International Search Report for PCT/FI2011/051129 dated Apr. 23, 2012.

Written Opinion for PCT/FI2011/051129 dated Apr. 23, 2012.

European Search Report for EP10196556 dated Jul. 29, 2011.

* cited by examiner

INTEGRATED PROCESS FOR PRODUCING BIOFUELS

The present application claims the benefit of priority under 35 U.S.C. §119(e) to U.S. Provisional Patent Application No. 61/459,963, filed on Dec. 22, 2010, the content of which is incorporated herein by reference in its entirety.

FIELD

The present invention relates to an integrated process for producing biofuels from lignocellulosic materials.

BACKGROUND

Lignocellulose is the most abundant biopolymer on earth. Lignocellulose is the major structural component of woody plants and non-woody plants such as grass. Lignocellulosic biomass refers to plant biomass that is composed of cellulose, hemicellulose, and lignin. Large amounts of lignocellulosic residues are produced through forestry, timber and pulp and paper industries and agricultural practices (straw, stover, bagasse, chaff) and many agroindustries. Also municipal waste contain fractions that can be considered as lignocellulose residues, such as paper or cardboard waste, garden waste or waste wood from construction. Due to high abundance and low price lignocellulosic residues are preferred materials for production of biofuels. In addition, dedicated woody or herbaceous energy crops with biomass productivity have gained interest as biofuel use.

The production of biofuels, especially ethanol, from lignocellulosic materials by microbial fermentations has been studied extensively. The greatest challenge for utilization of lignocellulosics for microbiological production of biofuels or biofuel feedstocks lays in the complexity of the lignocellulose material and in its resistance to biodegradation. In lignocellulose, cellulose (20-50% of plant dry weight) fibers are embedded in covalently found matrix of hemicellulose (20-40%), pectin (2-20%) and lignin (10-20%) forming very resistant structure for biodegradation. Further, the sugar residues of hemicellulose contain a varying mixture of hexoses (e.g., glucose, mannose and galactose), and pentoses (e.g., arabinose and xylose) depending on the biomass.

The pre-treatment of lignocellulosic material with high yield to sugars that are utilizable by micro-organisms represents one of the highest challenges. Significant cost reductions are needed in the costs of enzymes needed in hydrolysis of sugar polymers to sugar monomers that are utilizable by desired microorganisms. Further, the economically feasible production of biofuels from lignocellulosic materials requires efficient conversion of all the main carbohydrate constituents of this complex material to biofuels. The production of cellulosic ethanol includes two main challenges: traditional ethanol producing organisms such as brewer's yeast (*Saccharomyces*) or *Zymomonas mobilis* (bacterium) are not able to utilize pentose sugars which are carbon and/or energy sources for ethanol production. This leads to inefficient utilization of total sugars in lignocelluloses to ethanol. Wild-type strains of brewer's yeast (*Saccharomyces*) or *Zymomonas mobilis* cannot utilize polymeric sugars in lignocellulose as carbon and/or energy sources for ethanol production. The enzymes for hydrolysis of sugar polymers to monomers need to be bought, but the enzyme costs are presently too high. Genetically modified brewer's yeast or *Zymomonas mobilis* strains capable of utilizing xylose have been developed, but have not been proven to be robust enough for long term large-scale operations. Same applies to genetically modified brewer's yeast with cellulose utilization ability. Pentose-utilizing ethanol-producing bacteria or other yeasts than *Saccharomyces* do exist, such as *Pachysolen tannophilus, Pichia stipitis*, and *Candida shehate*, however their low ethanol tolerance, low robustness and high sensitivity to inhibitors have prevented their commercial utilization.

The enzymatic hydrolysis is typically performed in a separate step from biofuel production process by commercial enzymes bought and produced outside the actual biofuel production process.

Lignocellulose hydrolysates have been utilized also in the production of single cell oils. Lignocellulose hydrolysis has been typically carried out by pre-treating the lignocellulosic material to monomeric sugars prior feeding to bioprocess.

Patent publication US2009217569 describes single cell oil production from various lignocellulosic and other material hydrolysates, such as straw, wood, pulp and paper industry residues, recycled fibres, municipal waste, algae biomass. For manufacturing biofuel comprises treating source material with water, acid or alkali and contacting filtrate or precipitate with lipid-producing microorganism. Patent publication US2009064567 describes single cell oil production from cellulose material hydrolysates for biodiesel and jet biofuel production by *Stramenopiles*. US20090011480 describes single cell oil production by heterotrophically grown algae and fungi from depolymerised lignocellulosic materials, such as straw, wood, pulp mill waste, switchgrass. CN101148630 describes single cell oil production from wheat, corn or rice straw hemicellulose hydrolysates, obtained by steam explosion, by bacteria or fungi.

Further, in the prior art has been described lipid production directly from polymeric sugars in lignocellulose, such as xylan by Fall et al. (1984), or cellulose by Lin et al., (2010). US2010028484 describes single cell oil production from co-products, such as stillage or DDGS, from cornfeedstock based ethanol production.

WO2010042842 describes production of single cell oil from lignocellulose hydrolysates by mixed culture of microorganism(s) capable of degrading polymeric sugars in lignocellulose and at least one algae species. The culture is grown in successive aerobic and anaerobic cultivations, where fatty acids are produced from sugars and from anaerobic fermentation products. However, the process leads to low production efficiency of oil production from lignocellulose since fermentation products (alcohols etc.) are used as carbon sources in the lipid production.

WO2010006228 describes sequential production of biofuels from lignocelluloses. In first stage, anaerobic fermentation with organisms capable of producing alcohols from polymeric sugars in lignocellulose hydrolysates, in second stage, the spent culture medium, possibly containing at least one fermentation product, is treated with algae in order to accumulate single-cell oils.

SUMMARY

It is one object of the present invention to provide a solution to problems encountered in the prior art. Specifically, the present invention aims to provide a technically beneficial solution to problems encountered in biofuel production processes.

It is another object of the present invention to provide a technically beneficial solution to problems encountered in the large-scale production of biofuels. In particular it is an object of the invention to provide a solution to problems encountered in the large-scale production of biofuels by microbiological processes, such as fermentation of alcohols or aerobic fermentation of single-cell oil.

It is third object of the present invention to provide a technically beneficial solution to problems encountered in the large-scale production of ethanol or other alcohols, or mixes of alcohols.

It is yet another object of the present invention to provide a solution, which enables upgrading the economy of biofuel production.

It is yet another object of the present invention to provide a solution, which enables reducing the environmental burden.

The present invention aims particularly to work out problems related to the manufacture of transportation biofuel such as alcohols, biodiesel and/or renewable diesel, gasoline or jet-fuel.

To achieve these objects the invention is characterized by the features that are enlisted in the independent claims. Other claims represent the preferred embodiments of the invention.

The present invention is based on the finding that some lipid producing microorganisms produce efficiently lipids from polymeric sugars in lignocellulose material directly. It has been surprisingly found that in a single cell oil production process is produced a significant amount of exoenzymes. It was further discovered that these exoenzymes remain active and can be collected from the spent culture medium.

Furthermore, the invention is based on the finding that some organisms produce exoenzymes that have activity towards different polysaccharides.

In one aspect the present invention provides an integrated process, which comprises a first biotechnical process, which produces a component or starting material for biofuel and uses a microorganism capable of producing enzymes, and a second biotechnical process, which produces a component or starting material for biofuel. The process comprises that the microorganisms are allowed to produce component or starting material for biofuel and enzymes, or component or starting material for biofuel.

The enzymes can be recovered from microorganism culture, spent culture medium or supernatant.

The supernatant and microorganism cells are optionally separated from the microorganism culture. Biofuel(s) are recovered from microorganism culture and/or from microorganism cells. Typically the supernatant or a protein enriched fraction of the supernatant or a dilution of the supernatant comprising catalytically active enzyme(s) is introduced into the first and/or into the second biotechnical process, or feedstock for the process(es) is treated.

In an embodiment of the invention, one process produces lipids from polysaccharides (polymeric sugars) and simultaneously produces extracellular enzymes capable of depolymerisation of sugars. The enzymes are re-used in another process producing biofuel or biofuel feedstock by organisms typically incapable of utilizing polysaccharides.

The present invention offers the following advantages/solutions

More complete utilization of lignocellulosic materials for the production of biofuels.
Efficient utilization of hemicellulose-stream for biofuel production. Currently used ethanol producers are not able to utilize pentose sugars efficiently.
Production of valuable product, suitable for production of biofuels along with the production of enzymes.
Cost savings on enzyme costs. Production of enzymes required in the ethanol, single cell oil or butanol process on site. Reduces the need of enzyme treatment prior to use, such as stabilization.
Consolidated bioprocess for lipid production (enzymatic digestion and fermentation) reduces costs by diminishing or eliminating the need for enzyme produced in a separate refinery.
The enzyme stream (cultivation liquid) need minimal processing since aerobic/anaerobic process, reduces contamination risk.

Furthermore, the production of enzymes for hydrolysis of cellulose and/or hemicellulose on site is advantageous for several reasons and improves the economics of biofuel production:

reduced down-stream processing costs including water and enzyme stabilization,
decreased transportation and packaging costs,
decreased losses via direct transfer of enzymes to second biofuel production process,
decreased capital costs vs. dedicated (remote) facilities,
the utilization of same raw material or raw material from same source for enzyme production and biofuel production in direct induction and adaptation of enzymes to the raw material
straightforward process control and output tuning and improvement opportunities directly within the biorefinery in enzyme production and biofuel production.

DETAILED DESCRIPTION

Definitions

Figure 1:
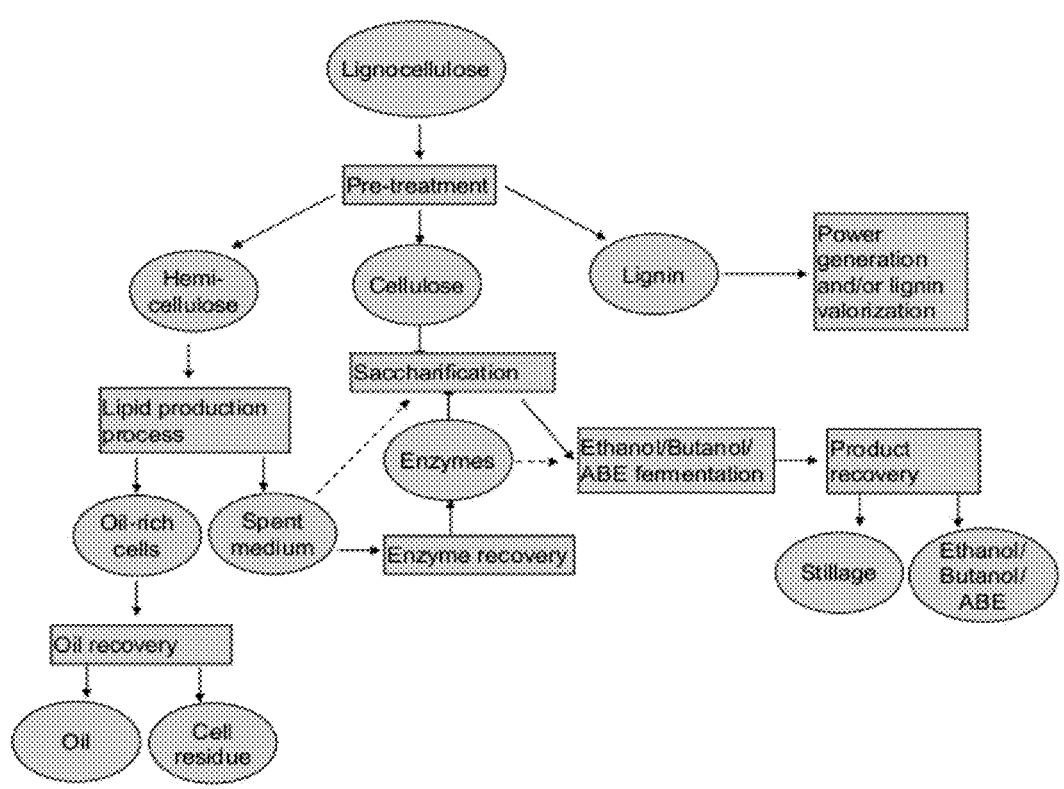
FIGS. 1 to 6 Process schemes

"A single cell oil production process" refers here to a process, comprising steps of forming or allowing the formation of a lipid synthesizing microorganism and allowing the thus obtained organism mass to produce and/or store (accumulate) lipid, recovering the cells from the liquid phase, and extracting or recovering the lipids from the cells. In certain cases, single cell oil can be also extracellular such as excreted or liberated from cells in culture medium during or after cultivation.

As described herein, the present invention uses preferably microorganisms capable of producing both lipids and enzymes. "A microorganism" refers in some embodiments of the invention to two or more microorganisms. In some embodiments, the enzymes are produced by one microorganism and the lipids by another microorganism. In some embodiments, more than one different strains of microorganisms are used for lipid and/or enzyme production.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols.

Preferred lipids in the present invention are fats, oils, waxes, acylglycerols and fatty acids and their derivatives, in particular triacylglycerols and wax esters.

In connection of this invention single cell oil is used as synonym for lipids and fat.

"Lipid recovery" refers to a process, in which the lipid (intracellular lipid) is recovered by mechanical, chemical, thermomechanical or autocatalytic methods or by a combination of these methods from the microorganism cells.

"Residual cell mass" stands for a solid, semi-solid or flowing material fraction, which contains microorganisms treated for the recovery of intracellular lipids By the term "alcohol" is meant as any organic compound in which a hydroxyl functional group (—OH) is bound to a carbon atom. "Alcohol" refers herein typically to organic compound containing hydroxyl group that is produced by microorganisms. Typical alcohols produced by microorganisms include but are not limited to ethanol, n-butanol, iso-butanol, propanol and/or iso-propanol. Alcohols are typically produced by anaerobic fermentations. Alcohols may be produced along with aldehydes, such as acetone, or organic acids, such as acetic acid and/or butyric acid, and gaseous products such as $CO_2$ and/or $H_2$.

Term "integrated process" or "process integrate" means a combination of at least two unit operations which exploit the interactions between different units in order to employ resources effectively, improve energy efficiency, improve material balance, maximize profit and/or minimize costs. At least one of the two unit operations in process integrate receives material and/or energy, and may be dependent on these, from the other unit operation. Process integration considers the interactions between different unit operations from the outset, rather than optimising them separately. Process Integration is not limited to the design of new plants, but it also covers retrofit design (e.g. new units to be installed in an old plant) and the operation of existing systems. Preferably the unit operations are situated in situ. However, this is not necessary and in some embodiments of the invention the unit operations are separately situated.

In an embodiment of the invention the enzyme production is initiated and/or maintained by adding an enzyme inducer into the microorganism culture. Generally this results in increased amount of produced enzymes. In particular in continuous cultivations it is important to maintain the amount of inducors on sufficient level to maintain the production of extracellular enzymes.

"A cultivation medium" refers here to a medium used for cultivating microorganisms. The cultivation medium comprises here typically polymeric sugars. The cultivation medium may be supplemented with minerals, micronutrients, macronutrients, growth factors and buffering agents.

The present invention provides a process for improving the efficiency and economics of biofuel production from lignocellulosic materials. The invention provides also a process for decreasing the input of externally produced enzymes for the hydrolysis of sugar polymers by utilizing microorganisms producing biofuels that possess capability of degrading polymeric sugars by exoenzymes. Further, the invention provides a process for producing valuable compounds suitable as biofuels or as raw materials for biofuel production along with the production of enzymes. The enzymes are preferably, at least partly, used on site and/or sold outside the process integrate.

The present invention relates to utilization of lignocellulosic material efficiently for lipid production of biofuels. The invention proves a process of producing biofuels, such as lipids, ethanol and butanol, from cellulose and/or hemicellulose fractions by microbiological processes in a process integrate. More specifically it provides a process for utilization of hemicellulose or cellulose fraction as a raw material for lipid production by microorganisms, which are able to utilize polymeric sugars by exoenzymes.

In one aspect the present invention provides a process for producing biofuels, such as lipids, ethanol and/or butanol, from lignocellulose materials or fractions thereof, such as from cellulose and/or hemicellulose fractions, by microbiological processes in a process integrate.

Further, the invention improves the overall efficiency of carbohydrate utilization by using different microorganisms in biofuel production from different fractions of lignocellulose (e.g. cellulose and hemicelluloses or fractions thereof): The organisms used for the production of biofuels from cellulose and hemicellulose are optimized in terms of their efficiency of utilizing sugars and producing biofuels from the said fraction.

In one embodiment of the invention, the present invention provides a process for the utilization of lignocellulose fractions, in particular hemicellulose and/or cellulose fractions as a raw material for lipid production by microorganisms, which are able to utilize polymeric sugars by exoenzymes.

In preferred embodiment of the invention, hemicellulose fraction from lignocellulose containing polymeric sugars is used for lipid production using oleaginous organisms that are capable of utilizing polymeric hemicellulose by producing exoenzymes. The enzymes recovered and/or enriched from spent culture medium from lipid production from hemicellulose have also cellulose degradation activity and can be used for cellulose hydrolysis in another process.

Another embodiment of the invention utilizes alcohol producing microorganisms for the utilization of lignocellulose fractions, in particular hemicellulose and/or cellulose fractions as raw materials, which are able to utilize polymeric sugars by exoenzymes. The exoenzymes involved in the utilization of polymeric sugars are re-used in the production of biofuel or biofuel feedstock production in a first or prior to a second biofuel production process. The polymeric sugar degrading exoenzymes produced by microorganisms (e.g. cellulases, hemicellulases, glucosidases, xylanases, arabinases, galactosidases, mannanases) that produce biofuels (e.g. lipid, ethanol, butanol, ABE=acetone-butanol-ethanol) from hemicellulose and/or cellulose in first bioprocess (bioprocess 1) can be reused in biofuel or biofuel feedstock production (e.g. ethanol, butanol, ABE, lipid) from cellulose and/or hemicellulose.

In one specific embodiment of the invention, the enzymes are partly recycled in the first biofuel production process which utilizes organisms capable of producing biofuels and enzymes In an embodiment of the invention the process includes in any case, one biofuel production process, preferably lipid production process, using sugar polymer from lignocellulose material (cellulose or hemicellulose) and organisms, preferably lipid-producing organisms, which have capability of utilizing these sugar polymers. Another embodiment of the invention utilizes alcohol producing microorganisms for the utilization of lignocellulose fractions, in particular hemicellulose and/or cellulose fractions as a raw materials, which are able to utilize polymeric sugars by exoenzymes. In addition, the exoenzymes capable of hydrolysing sugars are re-used in another bioprocess for the production of biofuels. The enzymes can be re-used, e.g to saccharify polymeric sugars prior to second biofuel production process or in (during) the second biofuel production process. The second biofuel production process can be single cell oil, ethanol, butanol or ABE production process. The processes are preferably integrated (biorefinery) or enzymes produced in first biofuel production process can be collected, purified and sold outside to be used in biofuel production from lignocellulose materials.

In an embodiment of the invention first biofuel production process (process 1) utilizes feedstock which contains polymeric sugars. Process 1 utilizes microorganisms that are capable of utilizing polymeric sugars by exoenzymes and capable of producing biofuels in the same process. Process 1 produces ethanol, butanol, acetone-butanol-ethanol, or lipids. Process 1 is preferably aerobic or aerated process producing lipids. Process 1 preferably uses microorganisms that are capable of utilizing both hemicellulose and cellulose by production of exoenzymes.

Exoenzymes produced in process 1 are recovered and re-utilized in hydrolysis of polymeric sugars for second biofuel production process (process 2) or in process 2.

In an embodiment of the invention process 2 utilizes microorganisms that are capable of producing biofuels from monomeric sugars but are not capable of producing exoenzymes to utilize polymeric sugars. Process 2 produces ethanol, butanol, acetone-butanol-ethanol, or lipids. Process 2 is preferably anaerobic process producing ethanol, butanol or acetone-ethanol-butanol.

Typical process options and raw materials, the raw materials may contain other components of lignocellulose such as lignin and/or pectin in addition to hemicellulose and/or cellulose:

Case 1: Process 1 uses hemicellulose; process 2 uses cellulose

Case 2: Process 1 uses cellulose; process 2 uses hemicellulose

Case 3: Process 1 uses cellulose; Process 2 uses cellulose

Case 4: Process 1 uses hemicellulose; Process 2 uses hemicellulose

Case 5: Process 1: uses a mix of hemicellulose and cellulose (any mix); Process 2: uses a mix of hemicellulose and cellulose (any mix)

Case 6: Process 1: uses a mix of hemicellulose and cellulose (any mix); Process 2 uses cellulose Case 7: Process 1: uses a mix of hemicellulose and cellulose (any mix); Process 2 uses hemicellulose.

In one preferred embodiment of the invention the enzymes capable of hydrolysing polymeric sugars are produced in an aerobic or aerated bioprocess which also produces biofuels or a starting material for biofuels, preferably lipids. The aerobic bioprocess enables efficient production of enzymes.

According to a preferred embodiment of the invention the hydrolysis and biofuel or biofuel feedstock production are carried out in a single step by utilizing microorganisms that are capable of both producing enzymes capable for hydrolysis of oligomeric sugars and production of biofuels. This kind of approach featuring cellulase (and/or hemicellulase) production, cellulose (and/or hemicellulose) hydrolysis and fermentation in one step is often called as consolidated bioprocessing. Consolidated bioprocessing offers the potential for lower cost and higher efficiency than processes featuring dedicated cellulase (and/or hemicellulase) production. This results in avoided costs of capital, substrate and other raw materials, and utilities associated with cellulase production. In addition, it offers possibility to obtain higher hydrolysis rates, and hence reduced reactor volume and capital investment, using consolidated bioprocessing. Consolidated bioprocessing reduces costs significantly by eliminating or at least diminishing the need for enzyme produced in a separate bioprocess.

In an embodiment of the invention the enzyme production and single cell oil production occur simultaneously or sequentially in any order. Typically the enzyme production is started earlier. The produced enzyme degrades the polymeric biomass in the cultivation medium thereby producing components for the growth of the microorganism.

In one embodiment of the invention, cellulose or hemicellulose fractions are divided into two parts. One part of the cellulose or hemicellulose, can be used to cultivate biofuel producing organisms possessing enzymatic capabilities for degradation of polymeric sugars. Enzymes can be recovered from spent culture medium, or spent culture medium comprising enzymes can be re-used for biofuel production from the second part of cellulose or hemicellulose. In one preferred embodiment of the invention lipids and alcohols are produced by microbiological processes, such as polymeric sugar utilizing microorganisms capable of accumulating lipids are used for one part of cellulose or hemicellulose. Alcohols are produced from other part of cellulose or hemicellulose treated by enzymes recovered from spent culture medium from first process using lipid-producers with capabilities to utilize polymeric sugars. In one embodiment of the invention, lipids and ethanol, lipids and butanol or lipid and acetone-butanol-ethanol (ABE) are produced. Similarly, ABE and lipids, ABE and ethanol, ethanol and ABE or ethanol and lipids can be produced.

The process as described herein is not limited to the use in the production of biofuels only. It can be combined with any kind of aerobic or anaerobic fermentation starting using polysaccharides as carbon and/or energy sources.

In one embodiment of the invention, a mixture of cellulose and hemicellulose is used for biofuel production by microorganisms possessing enzymatic capabilities to degrade polymeric sugars. Enzymes can be recovered from spent culture medium, or spent culture medium including enzymes can be re-used to hydrolyse cellulose or hemicellulose for biofuel production using organisms that are not capable of using polymeric sugars. In one preferred embodiment of the invention lipids and ethanol are produced by microbiological processes, such as polymeric sugar utilizing microorganisms capable of accumulating lipids are used for one part of cellulose or hemicellulose. Ethanol is produced from other part of cellulose or hemicellulose by treated by enzymes recovered from spent culture medium from first process using lipid-producers with capabilities to utilize polymeric sugars. Similarly, in yet in another embodiment of the invention, lipids and butanol or lipids and ABE are produced. Similarly, ABE and lipids, ABE and ethanol, ethanol and ABE or ethanol and lipids can be produced.

In one embodiment of the invention, the raw material for process contains polymeric sugars of both hemicellulose and cellulose (any mix) and utilizes microorganisms capable of producing exoenzymes for hydrolysis of polymeric sugars and biofuels (Process 1). The exoenzymes are in the spent culture medium are recovered and re-used in the saccharification of polymeric sugars of both hemicellulose and cellulose before or in another bioprocess (Process 2) producing biofuels using organisms that are not able to utilize polymeric sugars. As an example, hydrolysates containing polymeric sugars of hemicellulose and cellulose are divided into two fractions one fraction used for Process 1 and another fraction to Process 2.

In one embodiment of the invention the sugars used for Process 1 mainly-consist of hemicellulose, but also some cellulosic sugars in polymeric form, usually 0.5 to 20% (w/w), typically 0.5 to 10% (w/w). E.g. stream containing polymeric hemicellulose sugars is supplemented with a stream containing polymeric sugars of cellulose. Yet in another embodiment of the invention, the sugars used for Process 1 mainly consist of cellulose, but also some hemicellulosic sugars in polymeric form, usually 0.5 to 30% (w/w), typically 1 to 20% (w/w) E.g. stream containing polymeric cellulose sugars is supplemented with a stream containing polymeric sugars of hemicellulose.

In another embodiment of the invention, polymeric sugar utilizing microorganisms produce enzyme sets that have ability to utilize both hemicellulose and cellulose.

In one embodiment of the invention, the organism capable of utilizing polymeric sugars and producing biofuels or starting material for biofuels and another organism capable of producing biofuels or starting material for biofuels, but not able to utilize, polymeric sugars are added in the same reactor (mixed culture).

In one embodiment of the invention, the cells from biofuel production process using polymeric sugars are removed, and the spent culture medium as such, including enzymes capable of hydrolysing sugar polymers, are fed to another biofuel production process with organisms that are not capable of utilizing polymeric sugars.

The supernatant and cells need not to be separated completely. In some embodiments the supernatant comprises 1% to 30% of the cells of the original microorganism culture. In some embodiments the supernatant comprises 2 to 15%, in some embodiments 3 to 10%, in some embodiments 5 to 8% of the cells of the original microorganism culture.

In one embodiment of the invention, the same microorganism is used in the production of lipid and ethanol from lignocellulosic material. The lipid production is obtained in an aerated process (aerobic cultivation), which ethanol production is obtained in anaerobic or microaerobic cultivation.

By integrating aerobic and anaerobic bioprocesses significant decreases in raw material and chemical costs and increases total productivity of biofuels can be obtained compared to units operating independently.

By combining aerobic production of lipids as a first bioprocess (Process 1) and alcohols as a second bioprocess (Process 2) it is possible to transform most of the lignocellulosic material to compounds suitable for biofuel applications (alcohols, short C-chain solvents and lipids). Integration of a lipid and enzyme producing bioprocess to a fuel distillery producing ethanol, butanol, or ABE can increase total alcohol production capacity together with lipid production capacity.

In one embodiment of the invention aerobic process supplies process water to anaerobic process and vice versa. The recirculation of process water between aerobic and anaerobic bioprocesses decreases of microbial contamination risk since oxygen is very poisonous to anaerobic microbial strains, and on the other hand aerobic microorganisms do not grow well in anaerobic conditions.

After anaerobic process (Process 1 or 2) the solvents are traditionally separated from water fraction by distillation and suspended solids are separated after distillation from water by decantation. In one embodiment of the invention, the cell biomass and residual cellulosic polymers (and proteins if protein containing raw material has been used as raw material) are circulated to aerobic process. The spent culture medium, possibly containing, remaining sugars, such as unbroken oligomers, pentoses and cellobiose, diarabinose and xylobiose, can be re-circulated to aerobic process as well. If anaerobic process uses wild-type *Saccharomyces* yeasts for ethanol production these sugars are not utilized. In *Clostridium* based production of ABE, the bacterium can utilize pentoses a like typically lipid producing organisms in aerobic process.

According to one embodiment of the invention biofuels are produced in an integrated bioprocess in which lignocellulosic material is divided into two fractions one containing cellulose and another containing hemicellulose. The fractionation of lignocellulose to cellulose and hemicellulose fraction can be done by any suitable method. The hemicellulose and/or cellulose fraction can contain some lignin, or residues of lignin and/or pectin. In one embodiment of the invention, biofuels (lipid, ethanol, butanol or ABE) are produced from polymeric hemicellulose by utilizing organisms possessing enzymatic capabilities for degradation of polymeric sugars. Enzymes can be recovered from spent culture medium, or spent culture medium including enzymes can be re-used in the hydrolysis of polymeric cellulose for second bioprocess producing biofuels (ethanol, butanol, ABE, lipid). Alternatively, in yet another embodiment of the invention, biofuels are produced from polymeric cellulose by utilizing organisms possessing enzymatic capabilities for degradation of polymeric sugars. Enzymes can be recovered from spent culture medium, or spent culture medium including enzymes can be re-used in the hydrolysis of polymeric hemicellulose for biofuel production in a second bioprocess.

In practise, the separation efficiency of hemicellulose from cellulose is not 100% and the cellulose fraction contains some hemicellulose. The hemicellulose remains in cellulose fraction can be hydrolysed by enzymes recovered from used culture medium from first bioprocess (Process 1). Further, in practise the hemicellulose fraction can contain some polymeric cellulose, and if organisms are used which can utilize both polymeric hemicellulose and cellulose, both hemicellulase and cellulase enzymes can be recovered from spent culture medium and re-used in the second biofuel production process (Process 2).

Further, the degradation of hemicellulose and cellulose can involve same enzymes, such as, but not limited to cellobiases. Therefore, useful enzymes from spent culture medium from cultivation on polymeric hemicellulose can be recovered and re-used in the hydrolysis of polymeric cellulose.

FIG. 1 describes one embodiment of the invention in which aerobic lipid production and anaerobic alcohol production is integrated. In this concept lignocellulosic raw material for both bioprocesses can be pre-treated to form cellulose and hemicellulose fractions by any technology, such as, but not limited to hot water extraction, or organosolv methods. Aerobic lipid production process uses hemicellulose as raw material, while alcohol production uses cellulose as raw material. For aerobic lipid production process (process 1), lipid-producing microorganism(s) is chosen which produce at least hemicellulases, preferably both hemicellulases and cellulases.

According to the embodiment of the invention described in FIG. 1, aerobic lipid production and anaerobic alcohol production are integrated. Second bioprocess (Process 2) comprises anaerobic alcohol fermentation is faster, if cellobiase enzyme is added. The cellobiase enzyme is obtained preferable, at least partly, from spent culture medium from aerobic lipid production process, or alternatively or in addition commercial cellobiase can be used.

In second bioprocess comprising (process 2) alcohol production bioprocess, production strains which are not able to use pentoses or lignocellulosic disaccharides, such as Saccharomyces yeast, can be used. Also organisms capable of utilizing pentoses and/or polymeric sugars can be used, such as Clostridia for production of ethanol or ABE. Potentially, the spent culture medium and/or from Process 2 after product recovery can be recycled to lipid production bioprocess. The stillage, i.e. solid fraction from alcohol fermentation, from anaerobic process can be potentially treated in the same process pre-treatment or hydrolysis process than lignocellulose before feeding to aerobic lipid production. Further, the stillage and/or spent culture liquid (liquid phase) from anaerobic process can contain remains of cellulose, such as cellulose oligomers, which can act as indusor of cellulase production in lipid production process using organisms having cellulase activity. Further, the spent culture liquid from anaerobic process (process 2) can contain other organic compounds, such as organic acids, alcohols, glycerol, that can be converted to lipids in anaerobic bioprocess.

The spent culture medium from aerobic lipid production process (Process 1) can be recovered or concentrated to enrich enzymes, or used as such as dilution water of incoming cellulose hydrolysate to process 2.

Figure 2:
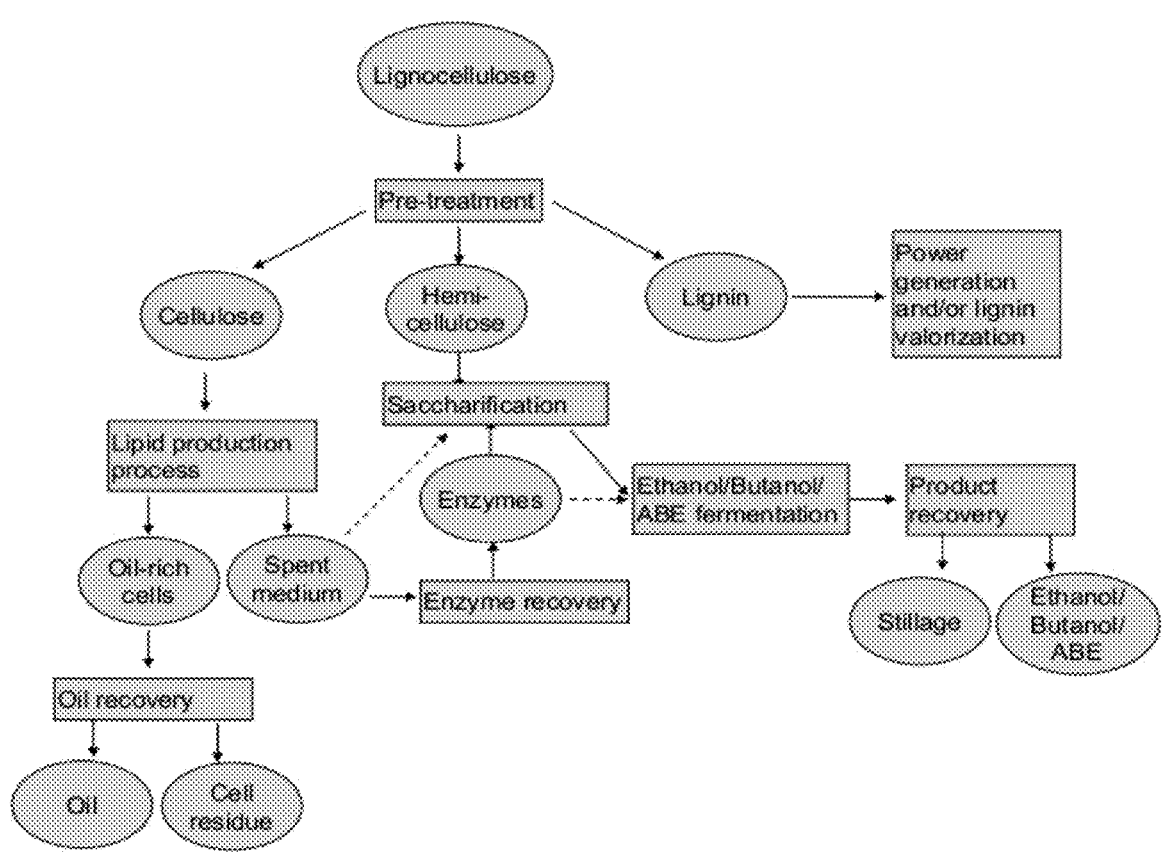

FIG. 2 describes one embodiment of the invention in which aerobic lipid production and anaerobic alcohol production is integrated. Aerobic lipid production process uses cellulose as raw material, while alcohol production uses hemicellulose as raw material. Aerobic lipid production process (process 1), lipid-producing microorganism(s) is chosen which produce both at least cellulases, preferably both hemicellulases and cellulases. The hemicellulase and/or cellulase enzymes are recovered and re-used for cellulose hydrolysis in another bioprocess which contains anaerobic fermentation of alcohols, such as ethanol, butanol or ABE, preferably production of ethanol or butanol.

In one embodiment of the invention, cellulose or hemicellulose fractions are divided into two parts. One part of the cellulose or hemicellulose, can be used to cultivate biofuel producing organisms possessing enzymatic capabilities for degradation of polymeric sugars. Enzymes can be recovered from spent culture medium, or spent culture medium including enzymes can be re-used for biofuel production from the second part of cellulose or hemicellulose. In one preferred embodiment of the invention lipids and ethanol are produced by microbiological processes, such as polymeric sugar utilizing microorganisms capable of accumulating lipids are used for one part of cellulose or hemicellulose. Ethanol is produced from other part of cellulose or hemicellulose by treated by enzymes recovered from spent culture medium from first process using lipid-producers with capabilities to utilize polymeric sugars. Similarly, in yet in another embodiment of the invention, lipids and butanol or lipid and acetone-butanol-ethanol are produced. Similarly, acetone-butanol-ethanol and ethanol can be produced.

Figure 3:
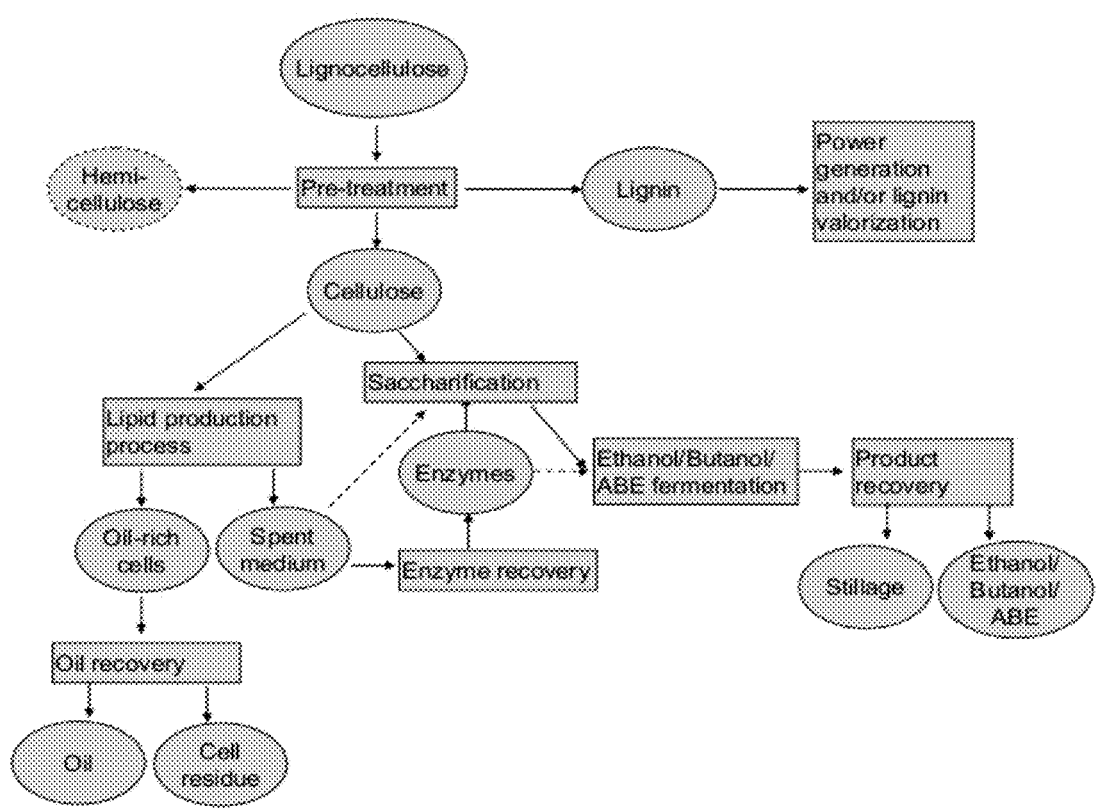
Figure 4:
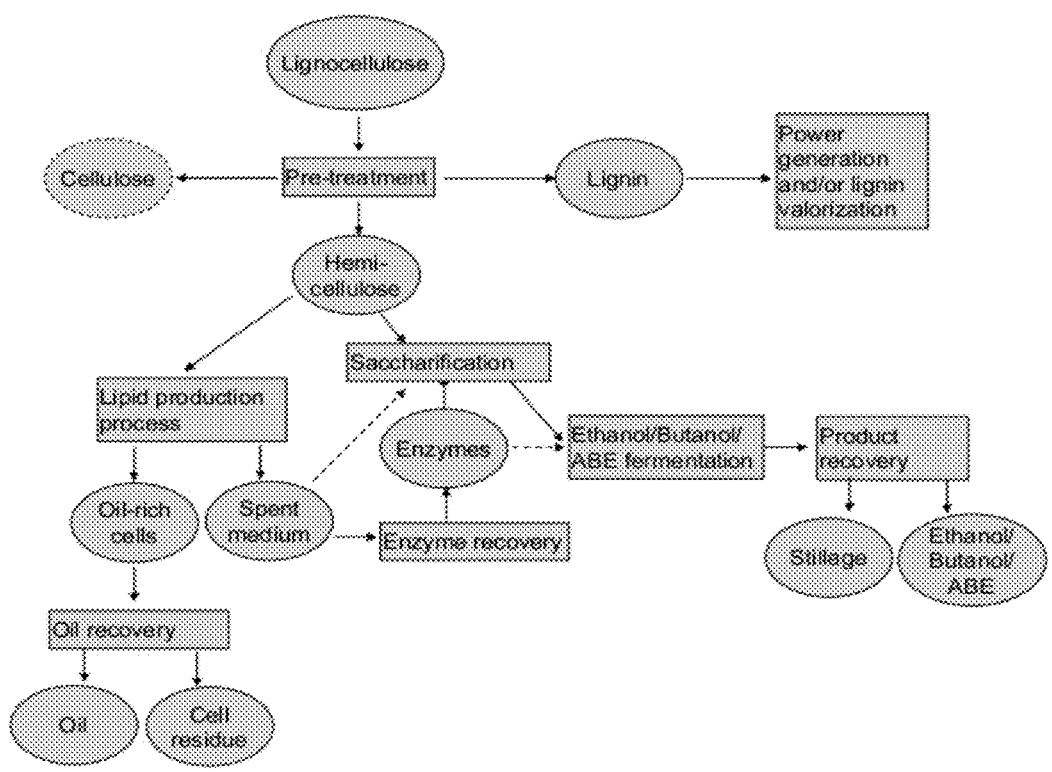

FIG. 3 describe an example, of biofuel production from cellulose, by an integrate of two bioprocesses. First bioprocess comprises aerobic lipid production which also produces exoenzymes capable for degradation of polymeric cellulose. The enzymes are re-used for cellulose hydrolysis in another bioprocess using cellulose which comprises anaerobic fermentation of alcohols, such as ethanol, butanol or ABE, preferably production of ethanol or butanol. FIG. 4 describe a similar bioprocess integrate for bioproduction of biofuels, but the process uses hemicellulose as raw material. Preferably first bioprocess is lipid production and second bioprocess is butanol or ABE production.

Therefore, any combination: lipid+ethanol; lipid+butanol; lipid+ABE, butanol+ethanol; ABE+ethanol; ethanol+ethanol etc., in any order, can be used in various embodiments of the invention.

According to one embodiment of the invention raw materials comprising cellulose or hemicellulose are divided into two fractions.

The process as described herein is not limited to the use in the production of biofuels only. It can be combined with any kind of aerobic or anaerobic fermentation starting using polysaccharides as carbon and/or energy sources.

In one embodiment of the invention, a mixture of cellulose and hemicellulose is used for biofuel production by microorganisms possessing enzymatic capabilities to degrade polymeric sugars. The cellulose and hemicellulose can be derived from the same material or are fractions from different raw materials The mixture can also contain some lignin or remains or degradation products of lignin and/or pectin. In one bioprocess, such organisms are preferably used which produce biofuel and also hemicellulases and cellulases. Enzymes can be recovered from spent culture medium, or spent culture medium including enzymes can be re-used to hydrolyse cellulose or hemicellulose for biofuel production using organisms that are not capable of using polymeric sugars. In one preferred embodiment of the invention lipids and ethanol are produced by microbiological processes, such as polymeric sugar utilizing microorganisms capable of accumulating lipids are used for one part of cellulose or hemicellulose. Alcohols, such as ethanol, butanol or ABE, is produced from other part of cellulose or hemicellulose treated by enzymes recovered from spent culture medium from first process using lipid-producers with capabilities to utilize polymeric sugars. Similarly, in yet in another embodiment of the invention, lipids and butanol or lipid and acetone-butanol-ethanol are produced. Similarly, acetone-butanol-ethanol and ethanol, ABE and lipids, ethanol and ABE, ethanol or lipids, can be produced.

In one embodiment of the invention, the raw material for the process comprises polymeric sugars of both hemicellulose and cellulose and utilizes microorganisms capable of producing exoenzymes for hydrolysis of polymeric sugars and biofuels (Process 1). The exoenzymes in the spent culture medium are recovered and re-used in the saccharification of polymeric sugars of both hemicellulose and cellulose before or in another bioprocess (Process 2) producing biofuels using organisms that may not be able to utilize polymeric sugars. As an example, hydrolysates containing polymeric sugars of hemicellulose and cellulose are divided into two fractions one fraction used for Process 1 and another fraction to Process 2.

Figure 5:
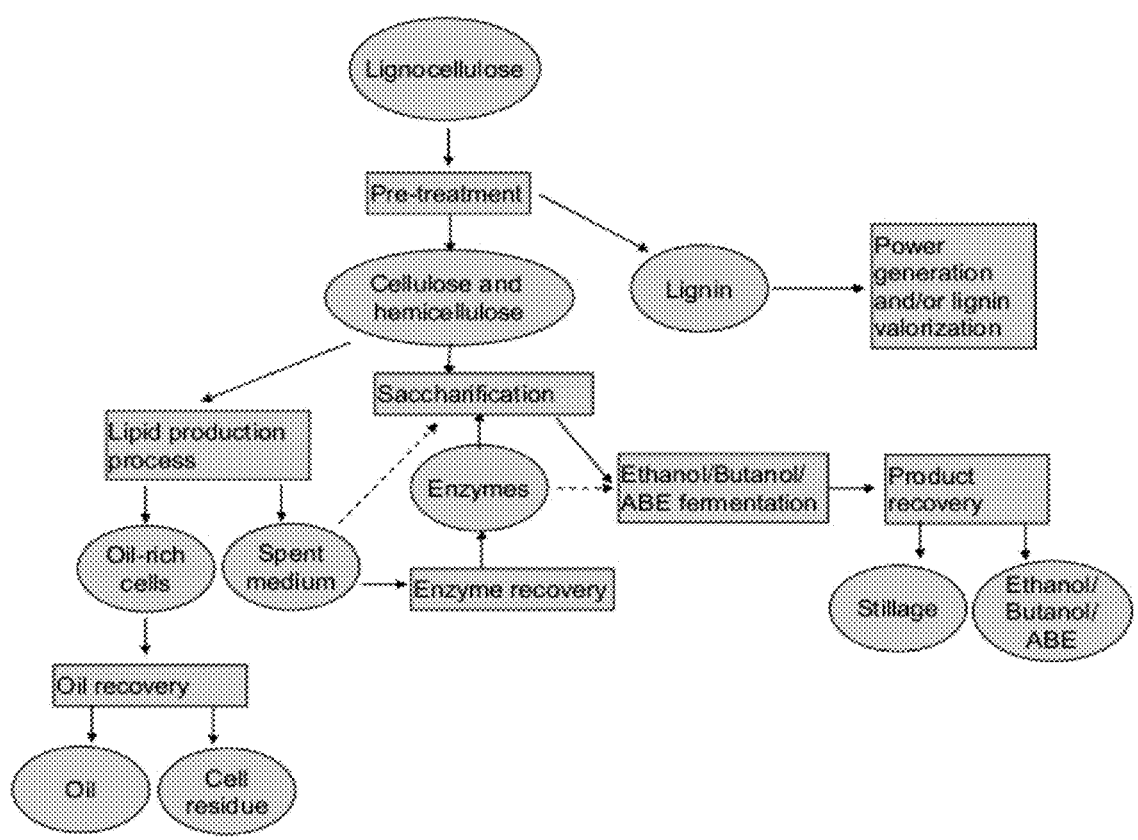

One specific embodiment of the invention utilizing a mixture of cellulose and hemicellulose from lignocellulosic raw material is shown in FIG. 5. In this embodiment of the invention aerobic lipid production process including organisms capable of utilizing polymeric sugars in cellulose and hemicellulose is integrated with anaerobic alcohol production process, such as ethanol, butanol or ABE production process (Process 2). The stillage and/or spent culture liquid can be recycled from alcohol production process to lipid production process, which can contain polymeric sugars that can act as indusors of production of hemicellulases and cellulases in lipid production process. Further, the spent culture liquid from anaerobic process (Process 2) can contain other organic compounds, such as organic acids, alcohols, glycerol, that can be converted to lipids in anaerobic bioprocess. Yet further, the spent culture medium or stillage from Process 2 can contain enzymes that are beneficial for Process 1.

Figure 6:
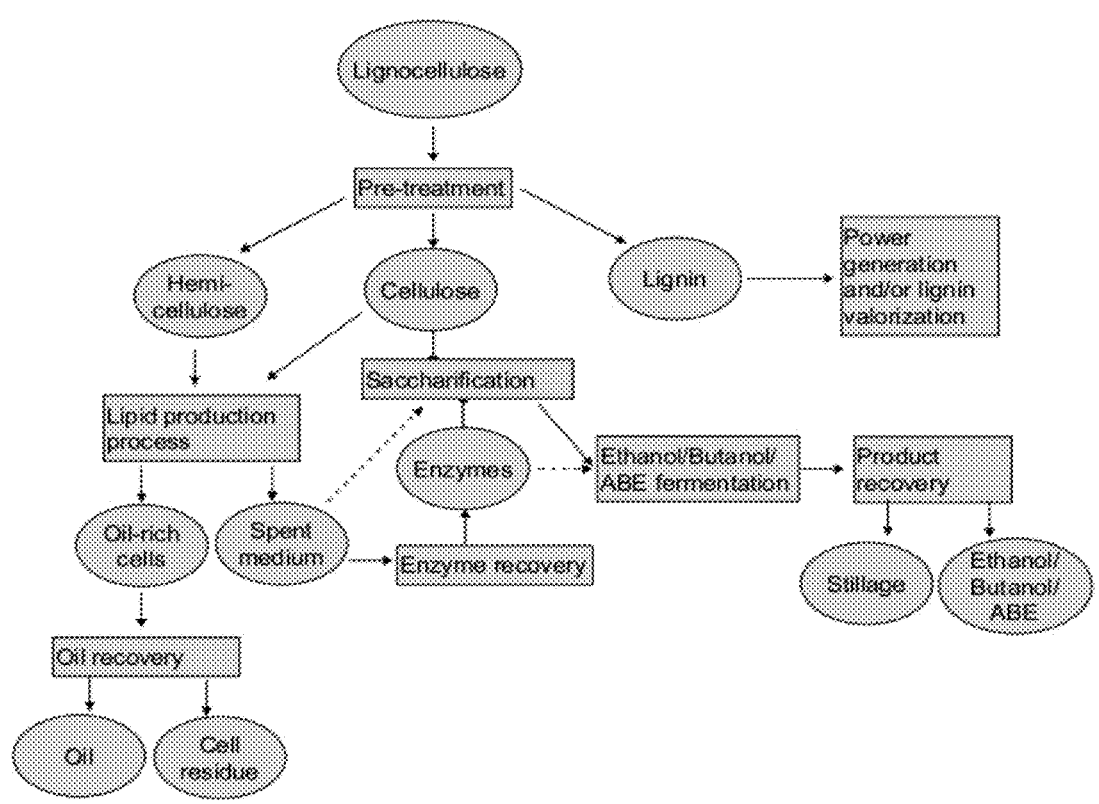

In one embodiment of the invention the sugars used for first bioprocess (Process 1) mainly comprise polymeric sugars' of hemicellulose, but also some cellulosic sugars in polymeric form. E.g. stream containing polymeric hemicellulose sugars is supplemented with a stream containing polymeric sugars of cellulose. First bioprocess uses microorganisms capable of producing exoenzymes for hydrolysis of polymeric sugars and biofuels. The second bioprocess (Process 2) uses raw material that comprise cellulose and microorganisms that are able to produce biofuels from sugars in cellulose, but which are not necessary capable of utilizing polymeric sugars. The exoenzymes from spent culture medium from Process 1 are used are recovered and re-used in the saccharification of polymeric sugars of both hemicellulose and cellulose before or in second bioprocess (bioprocess 2). FIG. 6 describes an example of such an integrated bioprocess where the first bioprocess is aerobic, microbial lipid production process and second bioprocess is an anaerobic, alcohol fermentation process. Most preferable, the second bioprocess is ethanol or butanol fermentation process.

Figure 7:
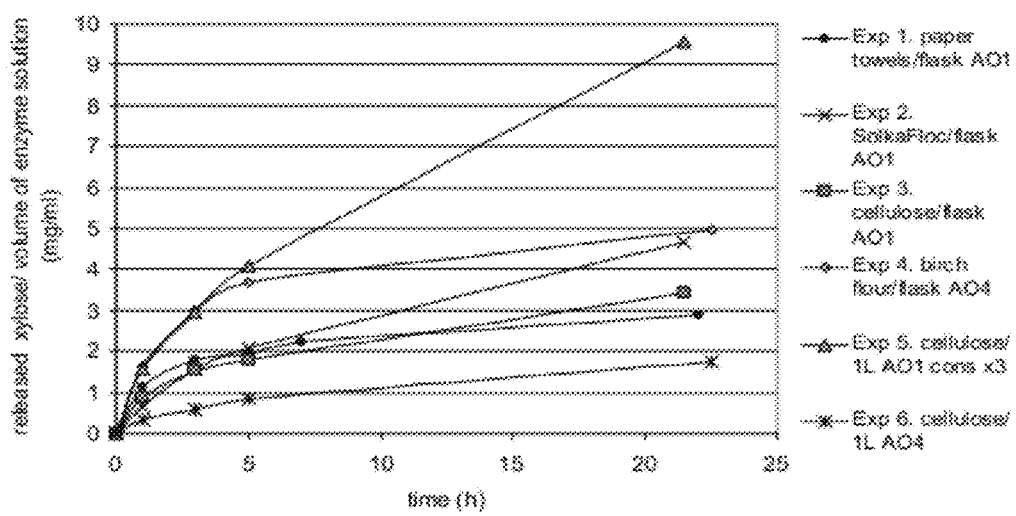
FIG. 7 Xylose released in the hydrolysis test per volume of culture broth. As substrate was used 200 mg birch wood xylan.

Yet in another embodiment of the invention, the sugars used for the first bioprocess (Process 1) mainly consist of polymeric sugars of cellulose, but also some hemicellulosic sugars in polymeric form. E.g. stream containing polymeric cellulose sugars is supplemented with a stream containing polymeric sugars of hemicellulose. First bioprocess uses microorganisms capable of producing exoenzymes for hydrolysis of polymeric sugars and biofuels. The second bioprocess (Process 2) uses raw material that comprises hemicellulose and microorganisms that are able to produce biofuels from sugars in hemicellulose, but which are not necessary capable of utilizing polymeric sugars. The exoenzymes from spent culture medium from Process 1 are recovered and re-used in the saccharification of polymeric sugars of both hemicellulose and cellulose before or in second bioprocess (bioprocess 2). FIG. 7 describes an example of such an integrated bioprocess where the first bioprocess is aerobic, microbial lipid production process and second bioprocess is an anaerobic, alcohol fermentation process. Most preferable, the second bioprocess is butanol and/or ABE fermentation process.

In another embodiment of the invention, polymeric sugar utilizing microorganisms produce enzyme sets that have ability to utilize both hemicellulose and cellulose.

In an embodiment of the invention, the organism capable of utilizing polymeric sugars and producing components for biofuels and another organism capable of producing components biofuels, but not able to utilize, polymeric sugars are added in the same reactor (mixed culture).

In an embodiment of the invention, the cells from biofuel production process with polymeric sugars are removed, and the spent culture medium as such, including enzymes capable of hydrolysing sugar polymers, are fed to another biofuel production process with organisms that are not capable of utilizing polymeric sugars.

More specifically, in an embodiment of the invention is used microorganisms, such as those capable of accumulating lipids or producing alcohols, such as ethanol, butanol or ABE, that can utilize pentose sugars thereby increasing the efficiency of lignocellulose utilization. Further, the organisms, such as lipid accumulating organisms or alcohol producing organisms, are also able to utilize polymeric sugars in cellulose and/or in hemicellulose by exoenzymes. The enzymes can be recovered from spent culture medium and used for hydrolysis of polymeric sugars in biofuel production processes, where microorganisms are not able to utilize polymeric sugars. In one specific embodiment of the invention, both bioprocesses utilize microorganisms that are able to utilize polymeric sugars and able to produce biofuels or starting material for biofuels.

In an embodiment of the invention, the same microorganism is used in the production of lipid and alcohol, in particular ethanol from lignocellulosic material. The lipid production is obtained in an aerated process (aerobic cultivation), which alcohol, in particular ethanol production is obtained in anaerobic or microaerobic cultivation.

In a one specific embodiment of the invention includes a process integrate of one of the bioprocesses in a process integrate is mesophilic bioprocess producing biofuels, and possibly enzymes, with operating temperature below 45° C., preferably below 40° C., while another bioprocess is thermophilic process producing biofuels, and possibly enzymes, with operating temperature above 45° C., preferably above 55° C. One example of such process integrate is a mesophilic aerobic lipid production with thermophilic anaerobic alcohol(s), such as ethanol, production process. The combination of mesophilic and thermophilic processes can be beneficial to the recycling and re-use of enzymes between bioprocesses. As an example, supernatant comprising enzymes, likely also comprising some cells, produced in the medium in mesophilic process are reused in a thermophilic process. The enzymes from mesophilic process may be thermostable to tolerate temperature in thermophilic process, while the residual cells in the supernatant are inactivated, and thus not able to grow in the thermophilic process. Alternatively, vice versa, the organisms grown in thermophilic temperature range, do not grow well in mesophilic temperature range in the next bioprocess and do not contaminate the process.

Recycling of Effluents and Biomass

The invention enables the recycling of effluents from one bioprocess to another bioprocess. In preferred embodiment of the invention, the ingrate uses at least one aerobic and one anaerobic bioprocess for the production of biofuels. This reduces the contamination risk when recycling effluents from aerobic process to anaerobic process. The aerobic bioprocess producing lipids can utilize compounds from effluent originating from anaerobic bioprocess as carbon and nutrient sources. Anaerobic bioprocess can be e.g. ethanol fermentation, butanol fermentation or acetone-butanol-ethanol fermentation (ABE-fermentation). These bioprocesses typically result in organic acids, such as acetic acid, butyric acid or acetaldehyde in fermentation effluent.

In addition to enzymes, the recycling of biomass and/or spent culture medium between the bioprocesses provide nutrients, minerals and/or growth factors, such as proteins, amino acids, vitamins, metabolites, coenzymes, which decrease the need of anabolism in microorganisms and therefore increase the microbial biofuel production, especially the production of lipids, which is an aerobic process step. In addition, the microbial cells from anaerobic process contains lipids, such as membrane lipids, which can be utilized by lipid production organisms, e.g. incorporated or transformed to triacylglycerols lipid producers. Lipid producing organisms can utilize the residual alcohols from the fermentation broth from alcohol production process after product recovery. In a specific embodiment of the invention, the alcohols from alcohols fermentation are not recovered, and the fermentation broth, containing alcohols and possible active enzymes, is fed to the aerobic lipid production process where they are converted to lipids.

The supernatant from lipid production in aerobic bioprocess or alcohol production in anaerobic bioprocess can be collected at different times in order to optimize the amount of enzymes for reuse in another bioprocess. In one embodiment of the invention, the biomass and/or supernatant is removed partly from the aerobic bioprocess during fermentation in order to optimize the activity of enzymes for re-use, and lipid content in biomass.

In one embodiment of the invention, the cell residue and other solid residues from lipid production is after lipid recovery or biomass from anaerobic alcohol production can be (thermo)mechanically, chemically or enzymatically treated before recycling back to the lipid production process or to anaerobic alcohol production bioprocess. If a cascade system is used the biomass can be recycled to any or all of the reactors in a cascade system. It is also possible to recycle biomass and/or fermentation broth between the cascade fermentors, with or without the treatment of cells in between. This can shorten the fermentation time by increasing the amount of biomass or active microorganisms and/or enzymes.

In one embodiment of the invention, the solid residues or biomass, spent culture medium and/or enzymes recovered or enriched from culture medium is recycled partly in the same bioprocess. This can improve the production of enzymes and/or biofuels in the bioprocess.

The recycling of biomass and/or spent culture medium can result in buildup of minerals, inert materials and other compounds and lead to inhibitions. Therefore, the amount of recirculation is optimized, and a certain amount of biomass and/or spent culture medium is removed time to time.

Pre-Treatment of Lignocellulose Before Fermentation

Pre-treatment of lignocellulose in order to improve the digestibility of polymeric sugar hydrolysing enzymes can be performed by any known method. The pre-treatment can include the fractionation (separation) of hemicellulose and cellulose and possible lignin by any known method. Choosing the correct pretreatment method is to a large extent dependant on the type of lignocellulosic feedstock to be used in the process. There are several methods/technologies that are only suitable for a certain type of raw material. Preferably, the separation of hemicellulose and/or cellulose in done with a method that produces hydrolysates which do not inhibit the growth of lipid producing microorganisms. The hemicellulose and cellulose fractions may contain sugars mainly or at least partly in polymeric form. One embodiment of the invention is to use hot water extraction to extract hemicellulose. In addition to hemicellulose, hot water extraction may remove minerals from lignocellulosic materials that are preferable in fermentation and this reduces the need of mineral additions in culture medium. In another embodiment, organic acid pre-treatment is performed, such as treatment with acetic acid, formic acid, ethyl acetate, lactic acid or malic acid or any combinations thereof. Yet in another embodiment of the invention, acid pre-treatment, such as with sulphuric acid, is performed. Also steam explosion with or without acid catalyst is used. Also methods such as organosolv pre-treatment, such as treatment with such as using ethanol methanol, acetone or any mixtures thereof, supplemented possibly with acid catalyst such as sulphuric acid or suphur dioxide ($SO_2$) can be used. Also other methods such as ammonia assisted pre-treatment, ammonia fibre expansion, ammonia recycle percolation or lime pre-treatments can be used. The lignocellulose material may be (thermo)mechanically treated, e.g. particle size reduced with any methods, such as, but not limited to, crushing or milling, prior to or in between of pre-treatment.

The purification and/or separation of cellulose, hemicellulose and lignin fractions may not be required before feeding biomass to a process that produces exoenzymes capable of hydrolysing polymeric sugars in lignocellulosic materials and produces biofuels, such as lipids.

Recycling of Biomasses

The microbial biomasses (cells), or biomass residues, such as biomass after lipid recovery, can be recycled from first bioprocess to the second bioprocess. In addition, or alternatively, microbial biomasses or biomass residues can be recycled from second bioprocess to the first bioprocess. The microbial biomasses can be potentially recycled with the supernatant. Microbial biomass can be treated (thermo) mechanically, enzymatically and/or chemically before feeding to the bioprocess. In one embodiment of the invention, the microbial biomass for recycle is treated in the same unit operation where lignocellulosic biomass is treated. In one embodiment of the invention, the microbial biomass for recycle undergoes same treatment than lignocellulosic biomass before feeding to a bioprocess, i.e. feeding to microbial production of biofuels or raw material for biofuel production. The recycled microbial biomass contains nutrients that can be beneficial for the bioprocess that it will be fed. The first bioprocess can be lipid or alcohol production, while the second bioprocess can be alcohol or lipid production.

The microbial biomasses, biomass residues, such as biomass after oil recovery, and supernatants from bioprocesses can be recycled between the bioprocesses. The supernatant and cells from bioprocesses contain nutrients and/or enzymes that can be recycled between bioprocesses and are advantageous for the bioprocess: Recycling biomasses and or supernatants can improve the overall product yield in bioprocesses and decrease the need of buying minerals or nutrients outside and can thus improve the economics of biofuel processes.

In one embodiment of the invention, at least part of the supernatant and at least part of the microbial biomass, or biomass residues, from bioprocess 1 is fed to the bioprocess 2.

In one embodiment of the invention, at least part the supernatant, and/or at least part of the cells and/or cell residues from bioprocess 2 can be recycled back to bioprocess 1.

If bioprocess 1 is an aerobic process, such as microbial, lipid production it can utilize organic residues, such as organic acids, alcohols or aldehydes, in the supernatant from an alcohol production process.

In an embodiment of the invention the process water or part it from the second biotechnical process after biofuel separation is recycled to dilution water of the raw material of the first biotechnical process and/or second biotechnical process, preferably to first biotechnical process.

In one embodiment of the invention, the supernatant or effluent from or after the recovery of alcohol from ethanol or butanol production process is recycled to a lipid production process. The lipid production process can utilize remains of ethanol or butanol in the supernatant or effluent for microbial growth and/or lipid production. Therefore, the ethanol or butanol recovery does not need to be complete, since remaining ethanol or butanol can be utilized for lipid production in subsequent biofuel production process by recirculating the effluent. This is advantageous, since the very high removal efficiency (yield) of products (ethanol or butanol) typically results in increased operational or capital cost. Allowing slightly lower product recovery yield can reduce operational or capital cost.

In another embodiment of the invention, the supernatant or effluent from or after the recovery of ABE from ABE fermentation process is recycled to a lipid production process. The lipid production process can utilize remains of ABE, in the supernatant or effluent for microbial growth and/or lipid production. Therefore, the ethanol recovery does not need to be complete, since remaining ABE can be utilized for lipid production in subsequent biofuel production process by recycling the effluent.

Raw Materials

The method can be applied to any lignocellulosic materials including woody plants or non-woody, herbaceous plants or other materials containing cellulose and/or hemicellulose: Materials can be agricultural residues (such as wheat straw, rice straw, chaff, hulls, corn stover, sugarcane bagasse), dedicated energy crops (such as switchgrass, *Miscanthus*, reed canary grass, willow, water hyacinth), wood materials or residues (including sawmill and pulp and/or paper mill residues or fractions, such as hemicellulose, spent sulphite liquer, waste fibre and/or primary sludge), moss or peat, microorganisms or municipal paper waste. Also low lignin materials, materials such as macroalgae or microalgae biomass can be used. In addition, the materials can be also hemicellulose or cellulose fractions from industrial practises. The invention can utilize any kind of cellulose fraction. The invention can use any kinds of hemicellulose fractions containing, e.g. but not limited to galactoglucomannan, xylan or arabinoxylan as main fractions. The raw materials or certain fractions, such as hemicellulose and/or cellulose, of raw materials from different origin, plant species, or industrial processes can be mixed together and used as raw materials for the bioprocesses according to the invention.

The hemicellulose and/or cellulose fraction containing polymeric sugars can be fed to the bioprocess that produces exoenzymes capable of hydrolysing polymeric sugars in lignocellulosic materials and produces biofuels, such as lipids or alcohols in any form, i.e. solid form or dissolved form or as partly solid and partly dissolved form.

In one embodiment of the invention, the lignocellulosic biomass is added as a solid form in the bioprocess producing exoenzymes capable of hydrolysing polymeric sugars in lignocellulosic materials and produces biofuels, such as lipids. In one embodiment of the invention the solid lignocellulose may have been mechanically treated to obtain smaller particle size, e.g. by milling or crushing, but has not been pre-treated to separate cellulose, hemicellulose or lignin fractions prior to fermentation. Yet in another embodiment of the invention the solid fraction of lignocellulose is, in addition to mechanical treatment to reduce particle size, treated with methods that have opened or loosened the structure of lignocellulose prior to feeding to bioprocess producing exoenzymes capable of degrading polymeric sugars and biofuels (Process 1). Such solid fraction of lignocellulose may contain cellulose and/or hemicellulose and lignin in polymeric form.

The lignin fraction, if fractionated from lignocellulose, can be used for any known purposes, such as but not limited to power and heat production, to production of biochemicals (bioplastics, resins), to structural biomaterials, to pyrolysis to hydro-deoxygenation or to gasification and Fischer-Tropsch synthesis of compounds that can be used as chemicals, biofuels and/or lubricants.

The advantage of the invention is that the process produces the exoenzymes needed by itself (in situ) without or reduced need of addition of other enzymes not produced by the strains used in the process described. The exoenzymes produced in one process producing lipids from cellulose and/or hemicellulose are recovered from the culture medium and used in integrated process to produce biofuel or biofuel feedstock with organisms that are not able to utilize polymeric sugars. In another embodiment of the invention the culture medium, from lipid production from polymeric sugars containing exoenzymes capable of degradation of polymeric sugars, after cell recovery is concentrated in enzymes or used without enrichment as a culture medium for biofuel or biofuel feedstock production from polymeric sugars by organisms that are not able to use polymeric sugars.

The raw materials for the production of biofuels according to the invention include those which contain preferably at least some polymeric sugars.

In the most preferred embodiment of the invention the raw material is lignocellulosic biomass or any fractions thereof.

In another embodiment of the invention, the raw material is starch or contains starch. Some examples of starch-containing materials include, but are not limited to corn, grains such as wheat and barley, tapioca, cassava, rice, potato, sweet potato and microalgae.

According to the invention the first bioprocess utilizes raw materials containing starch by using microorganisms that are able to utilize polymeric sugars in starch and produce biofuels. The starch hydrolysing enzymes in supernatant from first bioprocess are fed to the second bioprocess for microbial production of biofuels to hydrolyse the polymeric sugars starch. The second bioprocess utilizes microorganisms that are not able to utilize polymeric sugars in starch, or alternatively utilize microorganisms that are able to utilize polymeric sugars in starch. The introduction of enzymes with hydrolysis activity toward starch will enhance the starch hydrolysis for the second bioprocess.

Lignocellulose Hydrolysis

Cellulose does not typically dissolve in water in nature. The hydrolysis of solid cellulose requires typically three different types of enzymes: Endoglucanases, exoglucanases and β-glucosidases Endoglucanases (EC 3.2.1.4), operated mostly on amorfous part of cellulose, attack randomly on internal ponds of cellulose macromolecule. Exo-glucanases or cellobiohydrolases (EC 3.2.1.91) attacks on the end of cellulose chain hydrolyzing mainly one cellobiose unit at a time. Exoglucanases are able also to hydrolyse crystalline cellulose polymer. Finally, the hydrolysis of cellobiose to glucose monomers is done by β-glucosidase (EC 3.2.1.21).

Cellulose hydrolysis usually needs co-operation of many different cellulases. The amount of different analysed glycosylhydrolases is very high, over 90 different enzymes are already numbered (even more under study) on 14 different families as example cellobiohydrolase domains (CBH I, II), endoglucanese domains (EG I, II. III, IV, V) and betaglucosidase domains (BGL I, II).

For the total enzymatic hydrolysis of hemicellulose (xylans, arabinoxylans and glucomannans) several different enzymes are needed, which must be activated about the same time. First attack is typically done by enzymes such as endoxylanases (1,4-β-D-xylan xylanohydrolases), endoarabinases, and endomannanases (1,4-β-D-mannan mananohydrolases). For example *Trichoderma reesei* has at least 4 different endo-xylanases and one endo-mannanase.

Enzymes capable to hydrolyse hemicellulose oligomers after endo-hemicellulases operation are for example 3-xylosidase, β-arabinosidase, β-mannosidase and β-glucosidase (EC 33.2.1.21). For braking down the residual side-linkages included in oligomers α-glucuronidase (EC 3.2.1.139), α-arabinodase (EC 3.2.1.55) and α-D-galactosidase (EC. 3.2.1.22) are needed. For removal of acetyl-constituents is needed operation of esterases (EC 3.2.1.72).

Further, enzymatic hydrolysis of lignin requires activity of oxidative enzymes like lignin peroxidase (LiP EC 1.11.1.14), manganese-dependent peroxidase (MnP EC 1.11.1.13) and laccase (Ec 1.10.3.2). Modification of lignin needs co-operation of many enzymes, coenzymes and electron transport system between donors and final acceptors. The chemical structure and attachment of lignin to cellulose and hemicellulose is more important than the amount of lignin.

"ABE fermentation" or "ABE production" refers to a process where a mixture of acetone, butanol (n-butanol) and ethanol is produced by bacterial fermentation. In some cases iso-propanol is produced instead of acetone depending on the bacterial strain.

A process for production of alcohols typically comprises anaerobic cultivation of microorganisms in a bioreactor, typically in a fermentor. The microorganism is allowed to produce alcohol. The alcohol is collected from fermentation broth, typically by distillation. The alcohol, such as ethanol and/or butanol, recovered can be used as a biofuel. Ethanol needs typically to be dehydrated to 99.5% concentration prior to be used as biofuel, e.g. as gasoline and ethanol blends in vehicles.

Microorganisms

For the bioprocess (Process 1) containing feed including polymeric sugars suitable microorganisms can be any such microorganisms that are able to utilize polymeric sugars and able to produce compounds suitable for biofuel purposes. In preferred embodiment of the invention, lipid producing organisms used in the invention can be any organisms that can utilize polymeric sugars in hemicellulose and/or cellulose.

These organisms include but are not limited to bacteria, such as *Streptomyces* or *Bacillus*, filamentous fungi, such as *Aspergillus*, *Cephalosporium*, *Fusarium*, *Humicola*, *Microsphaeropsis*, *Nigrospora*, *Penicillium*, *Phanerochaete*, *Phomopsis*, *Rhizopus*, *Sclerocystis* or *Trichoderma*, such as *A. niger*, *A. terreus*, *A. oryzae*, *A. nidulans*, *F. oxysporum*, *Phanerochaete chrysosporium*, *R. oryzae* or *Trichoderma reesei*, yeasts, such as *Cryptococcus* or *Trichosporon*, such as *Cryptococcus albidus* or *Trichosproron cutaneum*. Oleaginous microorganisms that are genetically modified to be able to utilize polymeric sugars in cellulose and/or hemicellulose are also part of the invention. Further, organisms capable of utilizing polymeric sugars in cellulose and/or hemicellulose that are genetically modified to improved production of lipids are also included in this invention.

Microorganism capable of producing both lipids and enzymes is preferably a fungus, yeast or a bacterium, preferably belonging to a genus selected from the group of *Aspergillus*, *Humicota*, *Rhizopus*, and *Trichoderma*, or a yeast belonging to genus *Cryptococcus* or a bacterium belonging to *Streptomyces*.

In most preferable embodiment of the invention lipid producing microorganisms are used which can utilize polymeric sugars of both hemicellulose and cellulose, i.e. have both hemicellulose and cellulase activity. Such organisms include, but are not limited to filamentous fungi, such as *Aspergillus*, such as *Aspergillus terreus* and bacteria such as *Streptomyces*.

For second bioprocess (Process 2), utilizing in which polymeric sugars has been enzymatically digested, lipid producing organisms that are not able to utilize polymeric sugars can be used. However, process can also utilize organisms that are capable of utilizing polymeric sugars. Lipid producing organisms are selected from the group of bacteria, cyanobacteria, fungi such as yeasts and moulds (filamentous fungi), archaea or microalgae The microorganisms can readily accumulate lipids or have been genetically modified to accumulate lipids or to improve accumulation of lipids. Lipid producing organisms include, but are not limited to the, following organisms:

Microalgael species belonging to the genera comprising *Dunaliella*, *Chlorella*, *Botryococcus*, *Brachiomonas*, *Chlorococcum*, *Crypthecodinium*, *Euglena*, *Haematococcus*, *Chlamydomas*, *Isochrysis*, *Pleurochrysis*, *Pavlova*, *Prototheca*, *Phaeodactylum*, *Pseudochlorella*, *Parachlorella*, *Bracteococcus*, *Scenedesmus*, *Skeletonema*, *Chaetoceros*, *Nitzschia*, *Nannochloropsis*, *Navicula*, *Nannochloris*, *Scihizochytrium*, *Sceletonema*, *Thraustochytrium*, *Ulkenia*, *Tetraselmis* and *Synechocystis*.

Filamentous fungal species belonging to the following genera *Aspergillus*, *Mortierella*, *Chaetomium*, *Claviceps*, *Cladosporidium*, *Cunninghamella*, *Emericella*, *Fusarium*, *Glomus*, *Mucor*, *Paecilomyces*, *Penicillium*, *Pythium*, *Rhizopus*, *Trichoderma*, *Zygorhynchus*, *Humicola*, *Cladosporium*, *Malbranchea* and *Ustilago*.

Yeasts belonging to the following genera *Clavispora*, *Deparyomyces*, *Pachysolen*, *Kluyveromyces*, *Galactomyces*, *Hansenula*, *Saccharomyces*, *Waltomyces*, *Endomycopsis*, *Cryptococcus*, such as *Cryptococcus curvatus*, *Rhodosporidium*, such as *Rohodosporidium toruloides*, *Rhodotorula*, such as *Rhodotorula glutinis*, *Yarrowia*, such as *Yarrowia lipolytica*, *Pichia*, such as *Pichia stipitis*, *Candida* such as *Candida curvata*, *Lipomyces* such as *Lipomyces starkeyi* and *Trichosporon* such as *Trichosporon cutaneum* or *Trichosporon pullulans*.

Bacteria belonging to the following genera *Acinetobacter*, *Actinobacter*, *Alcanivorax*, *Aerogenes*, *Anabaena*, *Arthrobacter*, *Bacillus*, *Clostridium*, *Dietzia*, *Gordonia*, *Escherichia*, *Flexibacterium*, *Micrococcus*, *Mycobacterium*, *Nocardia*, *Nostoc*, *Oscillatoria*, *Pseudomonas*, *Rhodococcus*, *Rhodomicrobium*, *Rhodopseudomonas*, *Shewanella*, *Shi-*

*gella, Streptomyces* and *Vibrio*. Most preferably bacteria comprise *Rhodococcus opacus, Acinetobacter, Nocardia* or *Streptomyces*.

The organisms used for the production of ethanol can be selected from a group of bacteria, cyanobacteria, fungi such as yeasts and moulds (filamentous fungi), and microalgae, more preferably bacteria, filamentous fungi and yeasts. The microorganisms can readily produce ethanol or have been genetically modified to accumulate lipids or to improve accumulation of lipids. Ethanol-producing include organisms that are capable of utilizing monomeric or polymeric sugars in lignocellulosic materials. Ethanol-producing organisms include, but are not limited to the, following organisms:

Fungi such as yeasts belonging to the following genera *Saccharomyces*, like *S. cerevisiae* or *S. uvarum, Candida*, like *C. shehatae, Pachysolen*, like *P. tannophilus, Pichia*, like *P. stipitis* and *Schizosaccharomyces*, like *S. pombe.*

Filamentous fungi belonging to the following genera such as *Aurobasidium*, like *A. pullulans*, and *Fusarium*, like *F. avenaceum*, or *F. oxysporum*.

Bacteria belonging to the following genera such as *Bacteroides, Geobacillus, Clostridium* like *C. thermocellum* or *C. saccharolyticum, Erwinia*, like *E. chrysanthemi, Escherichia*, like *E. coli, Klebsiella*, like *K. oxytoca, Sarcina, Raoultella, Ruminococcus, Spirochaeta, Thermoanaerobacter*, like *T. ethanolicus, T. mathranii, T. thermohydrosulfuricus, Thermoanaerobacterium, T. aciditolerans, T. aotearoense, T. polysaccharolyticum, T. thermosaccharolyticum, T. zeae, Thermobrachium* like *T. cekere*, and *Zymomonas* like *Z. mobilis*.

The organisms used for the production of butanol, or acetone-butanol-ethanol, or iso-butanol-ethanol-acetone can be selected from a group of bacteria, cyanobacteria, fungi such as yeasts and moulds (filamentous fungi), and microalgae, more preferably bacteria, filamentous fungi and yeasts, more preferably bacteria. Butanol, or acetone-butanol-ethanol include producing organisms that are capable of utilizing monomeric or polymeric sugars in lignocellulosic materials. Butanol, or acetone-butanol-ethanol include producing organisms include, but are not limited to the, following organisms:

Bacteria belonging to the following genera such as *Clostridium*, like *C. acetobutylicum, C. beijerinckii, C. butyricum, C. aurantibutyricum, C. saccharoperbutylacetonicum* and *Escherichia*, like *E. coli*.

"Oleaginous microorganism" refers here as a microorganisms which accumulate at least 15% (w/w) of their biomass as lipid when cultivation in conditions suitable or optimal for lipid production.

"Lipid-containing single-cell mass" stands for an autotrophically, heterotrophically and/or mixotrophically formed single-cell mass and cellular mycelium with a lipid content of at least 3%, preferably at least 10%, preferably at least 15% (w/w) or more of dry matter of the microorganism.

Enzymes

The enzymes that are part of the invention include especially those which are able to convert sugars into a utilizable from to microorganisms. Typically such enzymes are hydrolytic enzymes, such as those which are able to convert sugar polymers to sugar monomers. Typically this is not performed by a single enzyme but a group of enzymes. Alternatively, enzymes capable of converting sugars to utilizable form to microorganisms include isomerases.

"Cellulase" or "cellulolytic enzyme" refers to a group of enzymes produced mainly by fungi, such as filamentous fungi or yeasts, bacteria, plants of by animals that catalyze the hydrolysis of cellulose, also called as cellulolysis. The EC number for cellulase enzymes is EC 3.2.1.4. Several different kinds of cellulases are known, which differ structurally and mechanistically. The general of cellulases include, based on the type of reaction catalyzed, endocellulases, exo-cellulases, cellobiases or beta-glucosidases, oxidative cellulases, and cellulose phosphorylases.

"Hemicellulase" refers to a group of enzymes produced mainly by fungi, such as filamentous fungi or yeasts, bacteria, plants of by animals that catalyze the hydrolysis of hemicellulose. For example, the enzymes involved in the hydrolysis of xylan include endo-xylanases, acetyl-xylanesterases, α-D-glucuronidases, α-L-arabinofuranosidases, ferulic acid esterases and β-Xylosidases. In addition, the enzymes involved in the hydrolysis of galactoglucomannan include endomannanases, acetyl-mannanesterases, α-Galactosidases, β-Glucosidases, β-Mannosidases. In addition the enzymes involved in the hydrolysis of arabinogalactan include β-Galactosidase and Endo-α-L-arabinanase. These enzymes can be found under the following EC numbers: EC 3.2.1.8, EC 3.2.1.37, EC 3.2.1.55, EC 3.2.1.99, EC 3.2.1.139, EC 3.2.1.78, EC 3.2.1.25, EC 3.2.1.22, EC 3.2.1.21, EC 3.2.1.89, EC 3.1.1.72, EC 3.1.1.6, EC 3.1.1.73.

"Hemicellulose" refers to a group of complex carbohydrates found in a lignocellulosic material that, with other carbohydrates (e.g., pectins), surround the cellulose fibres of plant cells. The composition of hemicelluloses is dependent on the plant type. Most common types of hemicelluloses include xylan, glucoronoxylan, glucomannan, galactoglucomannan, arabinoxylan, xyloglucan and arabinogalactan.

"Lignocellulosic material" or "lignocellulosic biomass" refers to biomass that is composed of cellulose, hemicellulose, and lignin or any fractions thereof.

"Saccharification" refers as hydrolysis of polymeric sugars to sugar monomers. Saccharification is typically achieved by the use of enzymes capable if hydrolysing polymeric sugars.

Bioprocesses

Microbial lipid production can be performed with any known method or a method developed in the future. Typically the microbial lipid production process includes cultivation of microorganisms in aerated bioreactors in submerged cultivation. Microorganisms are grown in liquid a culture medium comprising carbon and energy sources, such as hemicellulose and/or cellulose sugars, and macro- and micronutrients. Cultivation can be performed e.g. as batch cultivation, fed-batch cultivation, continuous cultivation. Cultivation can be also performed in a cascade process. In cultivation, microorganisms are let to grow and accumulate lipids intracellularly. Some microorganisms can also be able to excrete the lipids to culture medium.

The microbial lipid production process can be carried out also in reactors, where the amount of free water is low or where the production is carried out on a solid or semisolid surface. The cell mass or other biomass not dissolving in water, can be extracted with aqueous solutions in order to obtain enzymes into soluble form.

Microbial production of ethanol, butanol or acetone-ethanol-butanol performed with any known method or a method developed in the future. Typically the microorganisms are cultivated in a fermentor in submerged cultivation. Microorganisms are grown in liquid a culture medium consisting of carbon and energy sources, such as hemicellulose and/or cellulose sugars, and macro- and micronutrients. Cultivation can be performed e.g. as batch cultivation, fed-batch cultivation, continuous cultivation. Cultivation can be also performed in a cascade process.

Recovery of Enzymes from Spent Culture Medium

The enzymes can be recovered from microorganism culture, spent culture medium, supernatant and microorganism cells by any known and suitable method or by any suitable method developed in the future. The same applies also to methods by which the enzymes can be separated into fractions with the desired enzyme activities.

A preferred method for recovery for enzymes is a method by which the microorganism culture, the supernatant or any combination thereof can be treated by a person skilled in the art to achieve the recovery of the enzymes while maintaining their catalytic activity.

The supernatant and/or microorganism cells can be separated from the microorganism culture and used as an enzyme preparation or as a source of enzymes. Supernatant stands for a substantially cell-free fraction, which comprises the spent culture medium. Supernatant can be called also "fermentation liquid", "a liquid phase" or "culture both" or "cultivation broth".

The separation of the supernatant and the cells can be done by any suitable method maintaining the catalytic activity of the enzymes.

A method by which the microorganism culture or the supernatant or the enriched protein fraction comprising catalytically active enzyme(s) are recovered can be based on their molecular size, ionic behavior, solubility in water, solubility in different solutes or solubility in mixture solutes containing a buffering factor or a surface active factor or a surface-active compound or a salt.

The enzymes can be recovered from the culture medium by various procedures, including but not limited to procedures such as centrifugation, filtration, extraction, spray-drying, evaporation, or precipitation.

If needed the enzymes may be purified or isolated by various procedures including but not limited to chromatography, electrophoretic procedures, differential solubility, SDS-PAGE, or extraction.

The enzymes may be stabilized for example by salt, sugar or glycerol.

Furthermore, the enzymes may be formulated for the desired application.

"Extracellular enzymes" are enzymes excreted to the cultivation medium or released by cell lysis from the cells to the cultivation medium. Extracellular enzymes can be recovered from the supernatant.

In an embodiment of the invention the protein fraction is enriched in the supernatant. The enrichment can be carried out simple for example by concentrating the supernatant.

In some embodiments the protein fraction is enriched at least 10%, typically at least 20%, in various embodiments at least 30%, at least 40%, at least 50%, at least 60%, at least 70%, at least 80%, at least 90%, compared to the original liquid phase. Examples of suitable methods are methods based on ionic properties of proteins, molecule size, solubility, surface active properties or hydrophobic interactions. Preferably the recovery of enzyme fraction is carried out under conditions, where the temperature is 70° C. or lower.

In an embodiment of the invention the protein fraction in the supernatant is enriched at least 1 time (1×), typically at least 2 times (2×), preferably at least 3 times (3×). In some embodiments the protein fraction in the aqueous phase of the microorganism culture or in the supernatant is enriched at least 5 times, in some embodiments at least 10×, or 20× 30×, or 40×, or 50×, or 60×, or 70×, or 80×, or 90×, or 100× calculated as the enzyme activity per volume and/or per total protein.

Furthermore, in some embodiments the supernatant may be diluted before use in the integrated process.

Biofuel Production from Lipids

"Biofuel" refers to solid, liquid or gaseous fuel mainly derived from biomass or bio-waste and is different from fossil fuels, which are derived from the organic remains of prehistoric plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propyl-esters, from vegetable oil or animal oil of diesel quality. Biodiesel can also be produced from microorganism lipids, whereby microorganism lipid can originate from a bacterium, a fungus (a yeast or a mold), an algae or another microorganism.

"Renewable diesel" refers to a fuel which is produced by a hydrogen treatment of lipids of an animal, vegetable or microorganism origin, or their mixtures, whereby microorganism lipid can originate from a bacterium, a fungus (a yeast or a mold), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with fossil fuels. Suitable additives, such as preservatives and antioxidants may be added to the fuel product.

"Lubricant" refers to a substance, such as grease, lipid or oil, that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, cosolvents, and lubricity additives (see for example U.S. Pat. No. 7,691,792). Base oil for lubricant can originate from mineral oil, vegetable oil, animal oil or from a bacterium, fungi (a yeast or a mold), an algae or another microorganism. Base oil can also originate from waxes derived from biomass by gasification and Fischer-Tropsch synthesis. Viscosity index is used to characterise base oil. Typically high viscosity index is preferred.

The lipids produced according with the method described in this invention can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

Lipids produced with the method can be used as base oils for lubricants (lubrication oils) or as a starting material for production of base oils for lubricants The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty acid esters, phospholipids, glycolipids, sphingolipids and acylglycerols.

The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

Recovery of Oil

Microorganisms containing lipids may be separated from culture medium by any known methods, such as using a filtration or decanting techniques. Alternatively, centrifugation with industrial scale commercial centrifuges of large volume capacity may be used to separate the desired products.

In various embodiments of the invention, oil, or precursors for oil, may be recovered from cell biomass or culture broth using any method known in the art or developed in the future. Such methods, include, but are not limited to extraction with organic solvents. In various embodiments of the invention, microorganism cells may be disrupted to facilitate the separation of oil and other components. Any method known for cell disruption may be used, such as ultrasonication, osmotic shock, mechanical shear force, cold press, thermal shock, enzyme-catalyzed or self-directed autolysis.

The oil extracted cell residue can be used for energy production, e.g. combusted or treated with anaerobic digestion process, or utilized as animal feed. Oil-extracted cell residue, or a fraction of the cell residue, can also be recycled back to the bioprocesses to be used as a source of nutrients.

Recovery of Alcohols (Ethanol, Butanol, ABE)

The recovery of ethanol from fermentation broth can be done by any method. Traditionally distillation is used. When distillation is used as alcohol product separation technology, it is possible to get savings by combining the product recovery unit processes, such as distillation for alcohol production process and oil extraction for lipid production process including regeneration of oil extraction solvent, energetically together. The recovery processes can regenerate process heat which can be utilized in another unit process in production integrate, such as in enrichment or concentrating of hydrolysates or in other purposes.

In one embodiment of the invention, alcohols from anaerobic alcohol production process is used as extraction solvent possibly together with other solvents in lipid extraction from microbial cells. In one specific embodiment of the invention, ethanol from anaerobic fermentation process is used together with non-polar solvent, such as hexane to extract lipids from oil-rich cells formed in aerobic lipid production process.

In the recovery of alcohols, instead of distillation, which destroys the activity of most enzymes, even high vacuum is during distillation, other methods such as pervaporation or membrane technology can be used. The alcohol recovery may be performed with these methods from fermentation broth containing active enzymes and biomass during last steps of cascade fermentation or after batch fermentation. This enables to maintain enzyme activity in spent culture medium or those bound in sugar oligomers in order to recover, enrich them for re-use, such as recycle them to the bioprocess for the hydrolysis of lignocellulosic biomass. With membrane technology is possible to control the molecular size of molecules, such as enzymes, for recovery, enrichment and re-use. The recovery and re-use of enzymes can improve the efficiency and product yields in whole integrated system for production of biofuels.

To the process steps using elevated temperature, such as distillation, modification steps, such as catalytic modification of process water and ammonium or weak acids hydrolysis steps for separated biomass (increase yield, accelerate fermentation) can be added.

Separation of Butanol or ABE

The recovery of butanol and/or a mixture of acetone-butanol-ethanol from the fermentation broth can be done by any known method or any method developed in the future. Traditionally butanol has been recovered from fermentation broth from ABE fermentation by distillation, which is energy intensive. Alternative methods include, but are not limited to freeze crystallization of fermentation broth, gas stripping, pervaporation, membrane extraction, reverse osmosis, adsorption or liquid-liquid extraction.

In product recovery from alcohol fermentation process, technologies which enable maintenance of non-inhibitory product concentration and high productivity and high cell density (cell biomass concentration) can be applied. Such as the alcohol recovery can be done during fermentation or from a recycling stream in a fermentation, or by any other method.

According to the invention, such product recovery methods are preferred, which do not destroy the activity of hydrolytic enzymes in the culture broth, and thus enable the re-use of enzymes.

ILLUSTRATIVE EMBODIMENTS

In summary, various embodiments of the invention are described below with the aid of the following numbered clauses 1-29. The embodiments are illustrative and are not intended to limit the claimed subject matter.

Clauses

1. An integrated process comprising
   a first biotechnical process, which produces a biofuel and/or starting material for biofuel and uses a microorganism capable of producing enzymes, and
   a second biotechnical process, which produces a biofuel and/or starting material for biofuel,
   wherein the process comprises the steps
      cultivating said microorganisms and producing biofuel and/or starting material for biofuel and enzymes, or biofuel or starting material for biofuel,
      optionally separating supernatant and microorganism cells from the microorganism culture,
      separating biofuel or starting material for biofuel(s) from microorganism culture or from microorganism cells,
      introducing the microorganism culture, supernatant or a protein enriched fraction of the supernatant or a dilution of the supernatant comprising catalytically active enzyme(s) into the first and/or into the second biotechnical process, or treating feedstock for the process(es).

2. The process according to clause 1, wherein the product of the first process comprises alcohol(s) or lipids, preferably lipids.

3. The process according to clause 1 or 2, wherein the product of the second process comprises alcohol(s) or lipids, preferably alcohol(s).
4. The process according to any one of clauses 1 to 3, wherein the product of the process is recovered by using a method preserving the catalytic activity of the enzymes, preferably hydrolytic enzymes, in supernatant.
5. The process according to any one of clauses 1 to 4, wherein the alcohol comprises ethanol, butanol, iso-propanol-butanol-ethanol and/or acetone-butanol-ethanol.
6. The process according to any one of clauses 1 to 5, wherein the organic material fed to the lipid production process comprises at least 50% lignocelluloses or a fraction of lignocellulose, comprising preferably at least 10% polymeric sugars of the sugar fraction.
7. The process according to clause 6, wherein the lignocellulosic biomass or a fraction thereof, comprises agricultural residues, such as straw, bagasse or stalk, dedicated energy crops, such as switchgrass, *Miscanthus*, willow, water hyacinth or reed canary grass, micro or macroalgae, wood or forestry residues, pulp and paper industry fractions or residues, paper waste or municipal waste containing lignocellulose.
8. The process according to any one of clauses 1 to 7, wherein at least part of the organic material fed to the lipid production process comprises starch.
9. The integrated process according to any one of clauses 1 to 8, wherein the microorganism in the first process uses hemicellulose, or cellulose, both of them or a mixture of hemicellulose and cellulose or fractions thereof.
10. The integrated process according to any one of clauses 1 to 9, wherein the microorganism in the second process uses hemicellulose, or cellulose, both of them or a mixture of hemicellulose and cellulose of fractions thereof.
11. The method according to clause 1 to 10, wherein the microorganism capable of producing both lipids and enzymes is a fungus, yeast or bacterium, preferably belonging to a genus selected from the group of *Aspergillus, Humicola, Rhizopus*, and *Trichoderma*, or a yeast belonging to genus *Cryptococcus* or a bacterium belonging to *Streptomyces*.
12. The method according to any one of clauses 1 to 11, where the ethanol-producing microorganism is a yeast or bacterium, preferably a yeast belonging to a genus selected from the group of *Saccharomyces, Pichia*, and *Candida*, or a bacterium, preferably belonging to a genus selected from the group of *Zymomonas, Clostridia, Escherichia* and *Thermoanaerobacter.*
13. The method according to any one of clauses 1 to 12, where acetone-butanol-ethanol or iso-propanol-butanol-ethanol producing organisms belong to the genus *Clostridium.*
14. The process according to any one of clauses 1 to 13, wherein the enzymes comprise exoenzymes, preferably enzymes associated with hemicellulose and/or cellulose hydrolysis.
15. The process according to any one of clauses 1 to 14, wherein the enzymes comprise hemicellulases, xylanases, mannanases, arabinases, galactosidases, glucosidases, mannosidases, xylosidases, arabinofuranosidase, esterases. cellulases, endo-cellulases, exo-cellulases, cellobiases or beta-glucosidases, oxidative cellulases, or cellulose phosphorylase or any mixtures thereof.
16. The process according to one of clauses 1 to 15, wherein the need of certain enzymes obtained outside the integrated process is reduced by at least 5%, preferably at least 30% by the enzymes produced in the integrated process
17. Process according to one of clauses 1 to 16, wherein part of the enzymes are used outside the integrated process.
18. The process according to any one of clauses 1 to 17, wherein the microorganisms in the first biotechnical process are able to produce both hemicellulases and/or cellulases.
19. The process according to any one of clauses 1 to 18, wherein biomass from the first biotechnical process or part of it is recycled to the second biotechnical process.
20. The process according to any one of clauses 1 to 19, wherein biomass or part of it, supernatant and/or enzymes from the first biotechnical process or part of it/them is/are recycled to the first biotechnical process.
21. The process according to any one of clauses 1 to 20, wherein biomass, supernatant and/or enzymes from second biotechnical process or part of it/them is/are recycled back to first biotechnical process.
22. The process according to any one of clauses 1 to 21, wherein process water or part thereof from the second process after biofuel separation is recycled to dilution water of the raw material of the first biotechnical process and/or second biotechnical process, preferably to first biotechnical process.
23. Use of the lipids produced according to the process of any one of clauses 1-22 as biofuel, as a component of biofuel or as a starting material for biofuel production.
24. The use according to clause 23, wherein the biofuel is biodiesel or renewable diesel, gasoline and/or jet fuel.
25. Use of the alcohols(s) produced according to the process of any one of clauses 1-22 as biofuel, as a component of biofuel or as a starting material for biofuel production.
26. An enzyme preparation obtained by the process according to any one of clauses 1 to 22.
27. Use of the enzyme produced according to the process of any one of clauses 1-22 or the enzyme preparation according to clause 26 in an biofuel production process, preferably in an alcohol production process or in other application as an enzyme preparation or as a source of enzymes.
28. An integrated process system for lipid production and alcohol production, which comprises that the processes use lignocellulosic material or fractions thereof as raw material for lipid and alcohol production, and either or both of them produce enzymes to the alcohol production process.
29. An integrated process system for lipid production and alcohol production, which comprises that the processes use lignocellulosic material or fractions thereof as raw material for lipid and alcohol production, and lipid production process produces enzymes to the alcohol production process, preferably to ethanol production process.

It is an object of the following examples to illustrate the invention and shall not be construed as limiting the invention in any way.

EXAMPLES

The enzyme activities in spent culture broth from cultivations of fat-producing filamentous fungi were determined by hydrolysis tests with pure cellulose and xylan as substrates.

Methods

Sugar Definition:

In order to define the sugar concentration of a solution, the solution was made into a suitable dilution which was filtered through 0.2 µm prior to an HPLC analysis.

The column used in sugar definition was Shodex Sugar SP 0810 ion-exchanger in lead form (in stationary phase). The column dimensions were 8.0 mm (ID)×300 mm. The eluent was water (flow rate 0.6 ml/min) and the column temperature was 60° C. The detector was RI Shimatzu RID 10A and the pump was A6 and the autosampler was Shimatzu SIL 20A. The processing of results was conducted with Class-VP software.

Fatty Acid Analysis:

The fatty acid composition of samples was determined as in the method described by Suutari et al. (1990). Lipids in the samples were first hydrolyzed into free fatty acids, which were saponified into sodium salts thereof and thereafter methylated into methyl esters. The fatty acid methyl esters were analyzed gas chromatographically.

Protein Concentration Analysis:

The protein concentration of the culture broths were analysed after filtration of the broth through Whatman3 filter paper. The protein concentration was analysed according to the Bio-Rad Protein Assay (based on Bradford method).

Hydrolysis Tests:

The culture broth was filtered through Whatman3 filter paper before the hydrolysis test.

The xylanase activity was determined as follows. A 100 ml Erlenmeyer flask was used as the reaction vessel. It was filled with 20 ml 1% birch wood xylan (Sigma) solution in phosphate buffer (0.02 M, pH 5) as substrate, 10 ml filtered culture broth and 20 ml phosphate buffer (0.02 M, pH 5). The hydrolysis reaction was performed in an agitated (140 rpm) water bath at 50° C. Samples of 1 ml were taken from the reaction vessel directly after the addition of the culture broth and after 1, 3, 5, 21/23 hours. The hydrolysis reaction was stopped in the 1 ml sample by decreasing the pH by the addition of 50 µl of 1.33 M sulphuric acid. The released sugars were analysed by HPLC (see Sugar definition) with mannitol as standard.

Cellulase activity was determined with 1 g Whatman filter paper as cellulose substrate instead of xylan. The reaction volume was 50 ml containing 1 g Whatman filter paper in equal sized circles (ca. 5 mm diameter) as substrate, 10 ml filtered culture broth and 40 ml phosphate buffer (0.02 M, pH 5). The experiment was otherwise performed as with xylan.

Microorganism Strains:

Lipid producing microorganisms are generally available to the public from a plurality of recognized microbial culture collections, such as ATCC, DSM, etc. Various embodiments of the invention are discussed in the following examples by using microorganism strains as follows. *Aspergillus oryzae* DSM 1861, *Aspergillus oryzae* DSM 1864 and *Aspergillus terreus* DSM 1958.

Example 1

This example shows the enzymatic activity formed in the culture broth during the cultivation of *Aspergillus oryzae* with cellulose based material as carbon source for the production of lipids.

*Aspergillus oryzae* was cultured for lipid production on different cellulose based lignocellulose materials. The growth medium base contained per liter of water 40 g lignocellulosic material as carbon source, 0.5 g yeast extract, 1 g $MgSO_4.7H_2O$, 0.5 g $K_2HPO_4$, 1 g $KH_2PO_4$ and 0.2 g $CaCl_2.2H_2O$ and was supplemented with nitrogen source and trace metals.

Experiments 1-4 were performed as flask cultures. In experiments 1-3 the medium base was supplemented with 3 g $NaNO_3$ and 0.02 g $FeSO_4.7H_2O$ per liter and in experiment 4 the medium base was supplemented with 1 g $(NH_4)_2SO_4$ per liter. Parallel cultivations were done in 250 ml Erlenmeyer flasks containing 50-100 ml culture medium. Cultivation media were inoculated with 1% (v/v) *Aspergillus oryzae* spore suspension. The cultures were incubated at 28° C. temperature in orbital shaker (160 rpm) for 6 days.

Experiments 5-6 were performed as bioreactor fermentations.

In experiment 5 the culture medium base was supplemented with 6.5 g peptone, 0.00015 g $ZnSO_4.7H_2O$, 0.0001 g $CuCl_2.2H_2O$ and 0.00625 g $MnCl_2.4H_2O$ per liter growth medium base. The carbon source was cellulose which was added to the cultivation to give a final concentration of 55 g/l. For inoculation spore suspension was prepared by applying in total 24 ml of sterile water on two sporulating *A. oryzae* PDA petri plate cultures. The spores were suspended with a spreader and 1 L culture medium was inoculated with the suspension. The fermentation was performed at 28° C. temperature with 0.6 l/min aeration and 350-450 rpm agitation. Culture pH was 5.7 and it was adjusted with 3 M NaOH during the cultivation. Enzyme activities were determined after 233 h incubation.

In experiment 6 the growth medium base was supplemented with 1.46 g peptone, 0.00015 g $ZnSO_4.7H_2O$, 0.0001 g $CuCl_2.2H_2O$ and 0.00625 g $MnCl_2.4H_2O$ per liter. The carbon source was cellulose which was added to the cultivation to give a final concentration of 50 g/l. The cultivation medium was inoculated with 50 ml 48 h precultured *Aspergillus oryzae* suspension. The fermentation was performed in 1 L culture medium volume at 28° C. temperature with 0.8 l/min aeration and 350-450 rpm agitation. Culture pH was 5.7 and it was adjusted with 3 M NaOH during the cultivation. Enzyme activities were determined after 188 h incubation.

The cultures broths were separated and the protein concentration and the xylanase and cellulase activity assayed as described above.

TABLE 1

The nitrogen and carbon source, culture volume, as well as determined protein concentration.

| Exp | Carbon source | Nitrogen source | Culture volume (ml) | Protein conc. (mg/ml) |
|---|---|---|---|---|
| 1 | Hand tissues[1], ground with a Fritsch pulverisette-grinder | $NaNO_3$ | 50 | 0.19 |

TABLE 1-continued

The nitrogen and carbon source, culture volume, as well as determined protein concentration.

| Exp | Carbon source | Nitrogen source | Culture volume (ml) | Protein conc. (mg/ml) |
|---|---|---|---|---|
| 2 | SolkaFloc (purified cellulose) | NaNO$_3$ | 100 | 0.11 |
| 3 | Cellulose$^2$, treated by Wiley crushing, Alpine-sieve 0.3, Alpine-sieve 0.2 | NaNO$_3$ | 100 | 0.06 |
| 4 | Birch flour (ground with a Görgens Turborotor) | (NH$_4$)$_2$SO$_4$ | 100 | 0.18 |
| 5 | Cellulose$^2$, same treatment as in exp. 3 | Peptone | 1000 | 0.49$^3$ |
| 6 | Cellulose$^2$, same treatment as in exp. 3 | Peptone/ (NH$_4$)$_2$SO$_4$ | 1000 | 0.11 |

[1]Lotus Professional Hand tissue Standard, fiber raw material: recycled fibre, Georgia-Pacific Nordic.
[2]UPM, Wisabetula, Birch Bleached Hardwood Sulphate 790388 15-04-2008 Wisapulp. Hemicellulose ca. 15%.
[3]Broth concentrated three fold by ultrafiltration (10 000 Da filter in an Amicon Ultra 8200 stirred ultrafiltration cell from Millipore)
In experiment 6 the lipid content was measured to be 4%.

Figure 8:
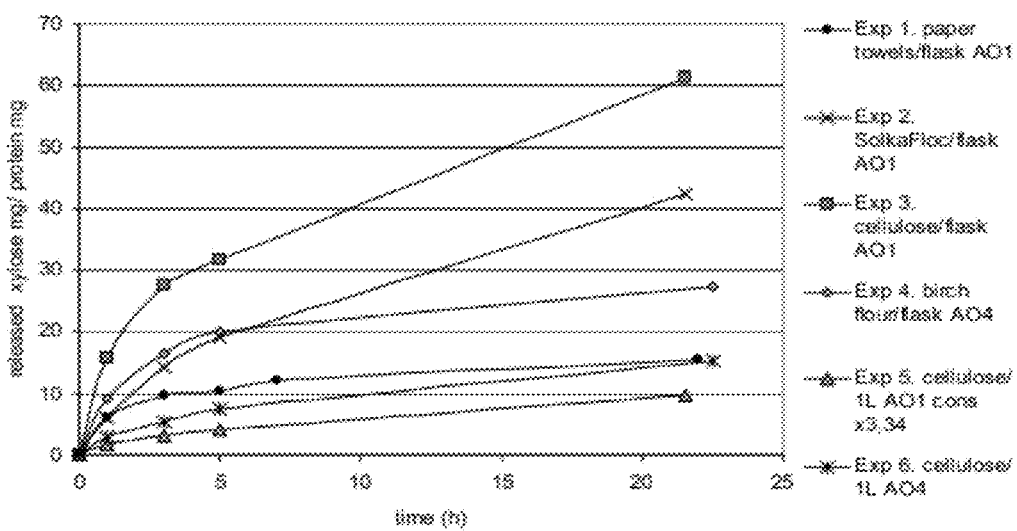
FIG. 8 Xylose released in the hydrolysis test per protein. As substrate was used 200 mg birch wood xylan.
Figure 9:
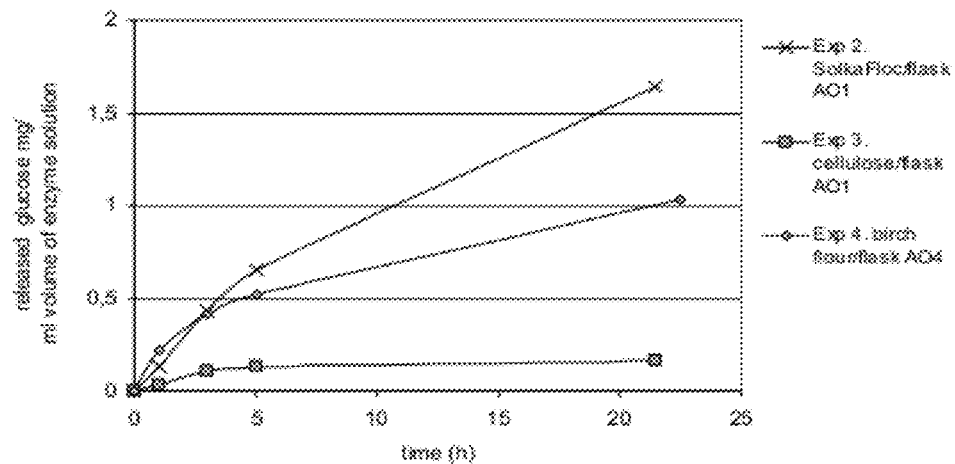
FIG. 9 Glucose released in hydrolysis tests per volume of culture broth. As substrate was used 1 g cellulose.
Figure 10:
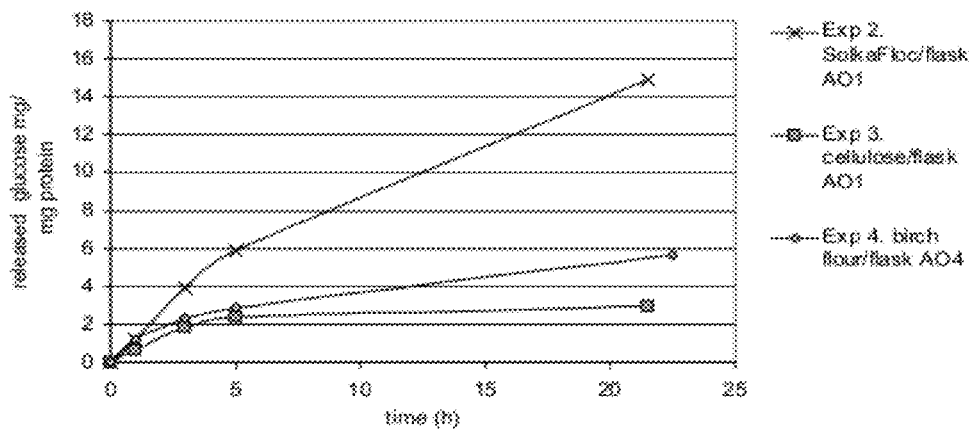
FIG. 10 Glucose released in the hydrolysis test per protein. As substrate was used 1 g cellulose.

The sugar released during the hydrolysis tests as milligram per milliliter culture broth and milligram per milligram protein as a function of time is presented in FIGS. 7 to 10. FIG. 7 shows the xylose released in the hydrolysis test per volume of culture broth. As substrate was used 200 mg birch wood xylan. FIG. 8 shows the xylose released in the hydrolysis test per protein. As substrate was used 200 mg birch wood xylan. FIG. 9 shows the glucose released in hydrolysis tests per volume of culture broth. As substrate was used 1 g cellulose. FIG. 10 shows the glucose released in the hydrolysis test per protein. As substrate was used 1 g cellulose.

All six tested culture broths from cultivations showed significant xylanase activity. Only three of the six culture broths showed signs of cellulase activity indicating a weak ability to produce these enzymes in specific conditions.

This example shows that *Aspergillus oryzae* can produce lignocellulolytic enzymes in the culture broth. The example shows that *A. oryzae* can have both xylan and cellulose degradation activity.

The enzyme production was selectively xylan degrading in most cases, three of the cultures showed weak cellulase activitie The re-use of hydrolytic enzymes produced by *A. oryzae* in lipid production can reduce the amount of commercial enzymes needed in the hydrolysis of lignocellulose or fractions thereof.

Example 2

This example shows the enzymatic activity formed in the culture broth during the cultivation of *Aspergillus terreus* with hemicellulose based material as carbon source for the production of lipids.

*Aspergillus terreus* was cultivated for lipid production on a wheat straw hemicellulose as carbon substrate in 2 liter volume in a bioreactor. The culture medium comprised of 50 ml Yeast Nitrogen Base w/o Amino Acids and Ammonium sulphate (Difco) 10× stock solution suspended in 2 L water and supplemented with per liter: 1.0 g yeast extract, 1 g (NH$_4$)$_2$SO$_4$, 1 g MgSO$_4$.7H$_2$O, 0.5 g K$_2$HPO$_4$, 1 g KH$_2$PO$_4$, 0.2 g CaCl$_2$.2H$_2$O and 2 g cellulose. The culture medium was inoculated with 150 ml 24 h precultured *A. terreus* culture. The fermentation was performed at 35° C. temperature with 3.0 l/min aeration and 200-430 rpm agitation. Culture pH was 5.7 and it was adjusted with 3 M NaOH during the cultivation. During the cultivation hemicellulose solution was fed to the fermentor. Enzyme activities were determined after 165 h incubation.

The culture broth was separated and it was partly concentrated by ultrafiltration in an Amicon stirred ultrafiltration cell with a 10 000 Da filter (Millipore). The protein and lipid concentration and the xylanase and cellulase activity were assayed as described as above.

The lipid content in the biomass containing fungal mycelium, residual hemicellulose and cellulose was 15% per dry weight. The protein concentration was 0.72 mg/ml in the unconcentrated culture broth and 2.15 mg/ml in the concentrated broth.

Figure 11:
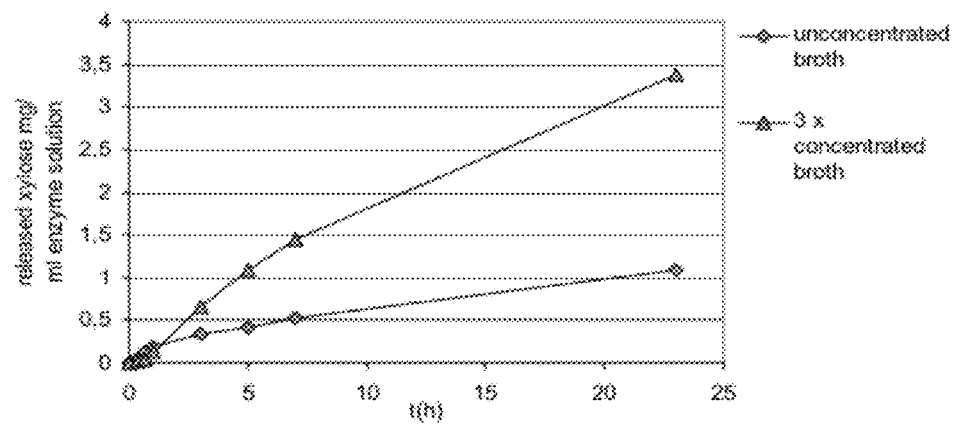
FIG. 11 Xylose released in the hydrolysis test per volume of culture broth. As substrate was used 200 mg birch wood xylan.
Figure 12:
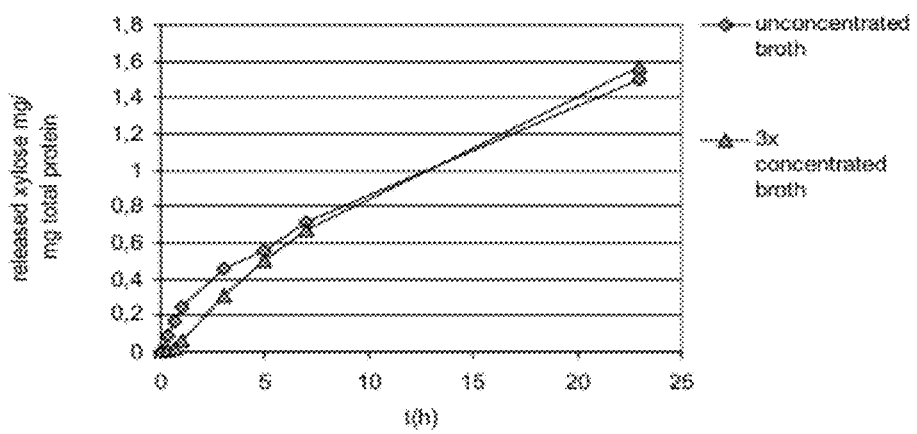
FIG. 12 Xylose released in the hydrolysis test per protein. As substrate was used 200 mg birch wood xylan.
Figure 13:
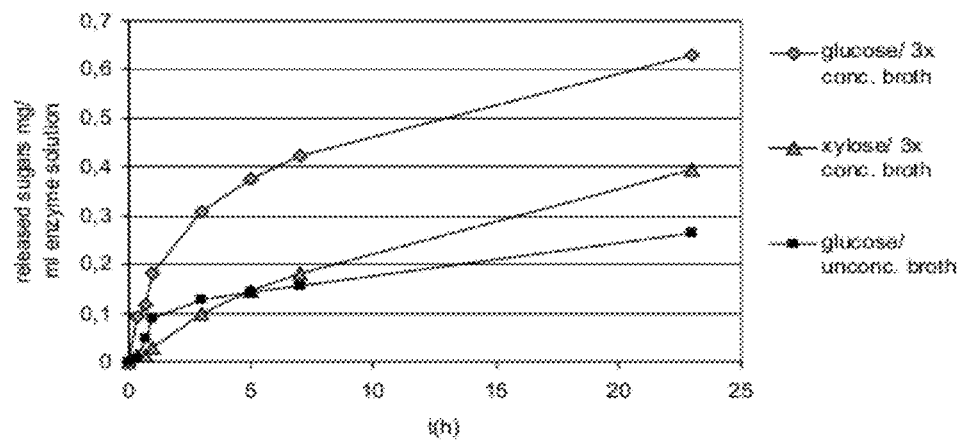
FIG. 13 Glucose released in hydrolysis tests per volume of culture broth. As substrate was used 1 g cellulose. Some xylose was released from the hemicellulose originating from the culture broth used.
Figure 14:
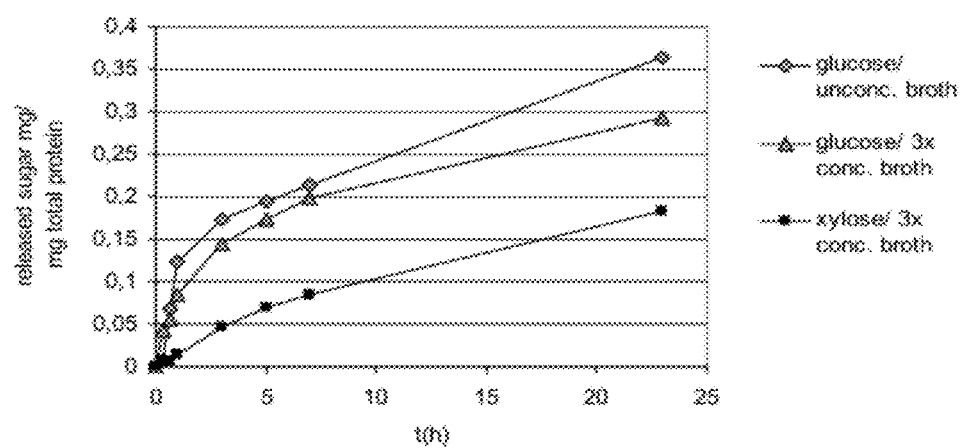
FIG. 14 Glucose released in the hydrolysis test per protein. As substrate was used 1 g cellulose. Some xylose was released from the hemicellulose originating from the culture broth used.

The sugar released during the hydrolysis tests as milligram per milliliter culture broth and milligram per milligram protein as a function of time is presented in FIGS. 11 to 14. FIG. 11 shows the xylose released in the hydrolysis test per volume of culture broth. As substrate was used 200 mg birch wood xylan. FIG. 12 shows the xylose released in the hydrolysis test per protein. As substrate was used 200 mg birch wood xylan. FIG. 13 shows the glucose released in hydrolysis tests per volume of culture broth. As substrate was used 1 g cellulose. Some xylose was released from the hemicellulose originating from the culture broth used. FIG. 14 shows the glucose released in the hydrolysis test per protein. As substrate was used 1 g cellulose. Some xylose was released from the hemicellulose originating from the culture broth used.

This example indicates that *Aspergillus terreus* can produce both lipid intracellularly and hydrolytic enzyme in the culture broth. The example shows that *A. terreus* produce enzymes, and excrete them to growth medium, that have both xylan and cellulose degradation activity. This enzyme can be separated, concentrated and used in hydrolysis of lignocellulosic material, such as material containing both polymeric cellulose and/or hemicellulose. The re-use of enzymes produced by *A. terreus* in lipid production can reduce the amount of commercial enzymes needed in the hydrolysis of lignocellulose or fractions thereof.

Example 3

The example shows integration of ethanol production with lipid production. Ethanol is produced from cellulose hydrolysed by enzymes in spent culture medium obtained from lipid production by mould.

In Example 3 it was shown that spent culture medium from cultivation and lipid production of *Aspergillus terreus* on wheat straw hemicellulose supplemented with cellulose contain enzymes, xylanases and cellulases capable of hydrolysis of lignocellulosic materials.

The spent culture medium is in this cultivation used to hydrolyse cellulose. Pure cellulose or wheat straw cellulose is added to the spent culture medium, treated by ultrafiltration in an Amicon stirred ultrafiltration cell with a 10 000 Da filter (Millipore), from cultivation and lipid production of *A. terreus* on wheat straw hemicellulose supplemented with cellulose. The solution is incubated at 30-70° C. for 16-200 h for saccharification of cellulose. After saccharification, nutrients (NH4)2HPO4 (0.5 g/L), MgSO4.7 H2O (0.025 g/L) and yeast extract (1.0 g/L) is added to the solution and the solution is inoculated with *Saccharomyces* cerevisiae yeast. *S. cerevisiae* is cultivated from 48 to 120 h at 36° C. maintaining pH at between 5.0 and 6.5 anaerobically. After cultivation (fermentation) cells are removed from culture medium by filtration through 0.2 µm or 0.45 µm filter, and/or by centrifugation at 5000×g for 5 min. The ethanol concentration from culture medium can be measured by gas chromatography or liquid chromatography such as HPLC.

Example 4

The example shows integration of acetone-ethanol-butanol (ABE) and lipid production processes. ABE is produced from wheat straw hemicellulose and/or cellulose hydrolysed by enzymes in spent culture medium obtained from lipid production by mould.

Hemicellulose and/or fraction from wheat straw is divided into two fractions. One fraction is used to produce lipids by *A. terreus* mould as described in example 3. Other fraction is used to produce ABE by *Clostridium acetobutylicum* bacteria.

In Example 3 it was shown that spent culture medium from cultivation and lipid production of *Aspergillus terreus* on wheat straw hemicellulose supplemented with cellulose contain enzymes, xylanases and cellulases capable of hydrolysis of lignocellulosic materials.

The spent culture medium is in this cultivation used to hydrolyse wheat hemicellulose. Wheat straw hemicellulose is added to the spent culture medium, treated by ultrafiltration in an Amicon stirred ultrafiltration cell with a 10 000 Da filter (Millipore), from cultivation and lipid production of *A. terreus* on wheat straw hemicellulose supplemented with cellulose. The solution is incubated at 30-70° C. for 16-200 h for saccharification of hemicellulose. After saccharification, yeast extract (1.0 g/L) is added to the solution and solution is sterilized at 121° C. for 15 min. After sterilization and cooling to room temperature minerals, buffer, and vitamins is added to the medium e.g. according to P2 medium which is described in Baer et al. (1987). The medium is placed in anaerobic bottle or jar and inoculated with *Clostridium acetobutylicum* bacteria. The culture is incubated 34 to 90 h at 35° C. maintaining pH at between 5.0 and 5.5. After cultivation (fermentation) cells are removed from culture medium by filtration through 0.2 μm or 0.45 μm filter, and/or by centrifugation at 5000×g for 5 min. The acetone, butanol and ethanol concentrations from culture medium can be measured by gas chromatography or liquid chromatography such as HPLC.

Example 5

This example shows the enzymatic activity formed in the culture broth during the cultivation of *Aspergillus oryzae* with hemicellulose based material as carbon source for the production of lipids.

*Aspergillus oryzae* was cultivated for lipid production on a wheat straw hemicellulose as carbon substrate in 2 liter volume in a bioreactor. The culture medium comprised of 50 ml Yeast Nitrogen Base w/o Amino Acids and Ammonium sulphate (Difco) 10× stock solution suspended in 2 L water and supplemented with per liter: 1.0 g yeast extract, 1 g $(NH_4)_2SO_4$, 1 g $MgSO_4 \cdot 7H_2O$, 0.5 g $K_2HPO_4$, 1 g $KH_2PO_4$ and 0.2 g $CaCl_2 \cdot 2H_2O$.

The culture medium was inoculated with 200 ml 72 h precultured *A. oryzae* culture. The fermentation was performed in 2 L cultivation medium volume at 30° C. temperature with 3.0 l/min aeration and 200-410 rpm agitation. Culture pH was 5.7 and it was adjusted with 3 M NaOH during the cultivation. During the cultivation hemicellulose solution was fed to the fermentor. Enzyme activities were determined after 144 h incubation.

The culture broth was separated and the protein concentration and the xylanase and cellulase activity assayed as described above. The lipid content in the biomass was containing fungal mycelium and residual hemicellulose 21% per dry weight. The protein concentration was 0.61 mg/ml in the unconcentrated culture broth and 1.65 mg/ml in the concentrated broth.

Figure 15:
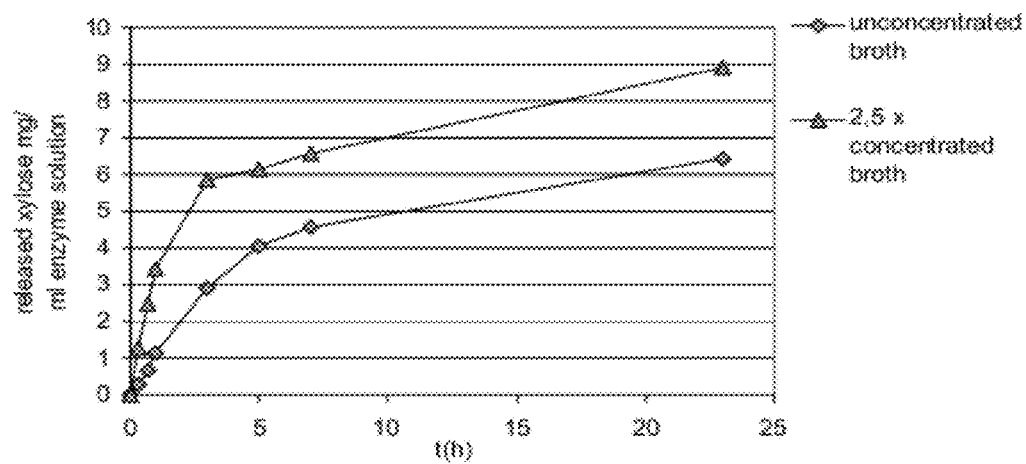
FIG. 15 Xylose released in the hydrolysis test per volume of culture broth. As substrate was used 200 mg birch wood xylan.
Figure 16:
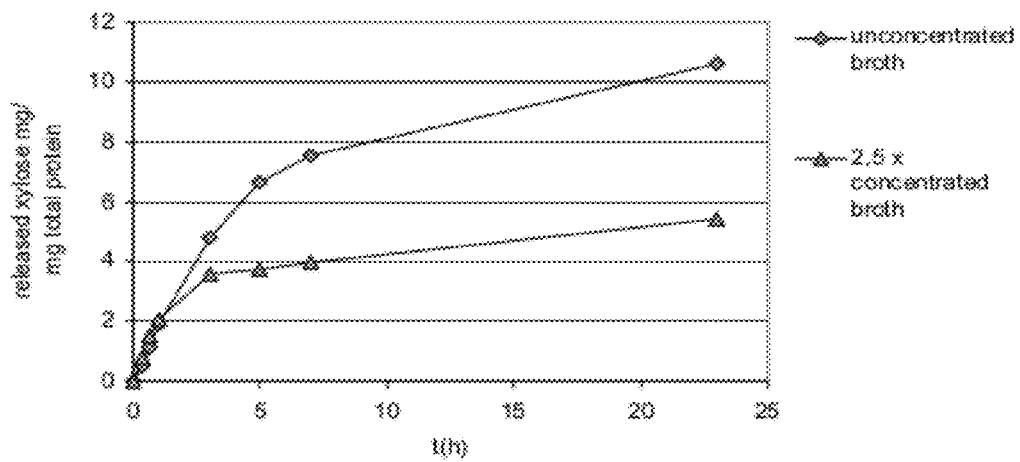
FIG. 16 Xylose released in the hydrolysis test per protein. As substrate was used 200 mg birch wood xylan.
Figure 17:
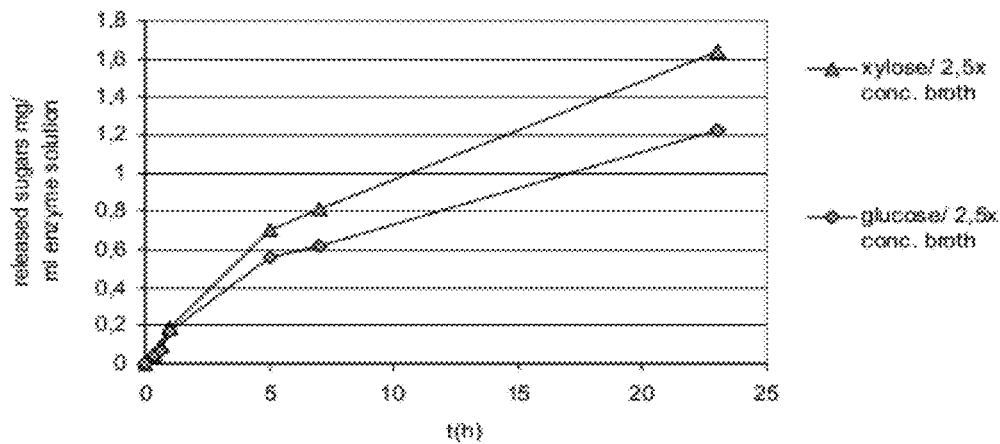
FIG. 17 Glucose released in hydrolysis tests per volume of culture broth. As substrate was used 1 g cellulose. Some xylose was released from the hemicellulose originating from the culture broth used.
Figure 18:
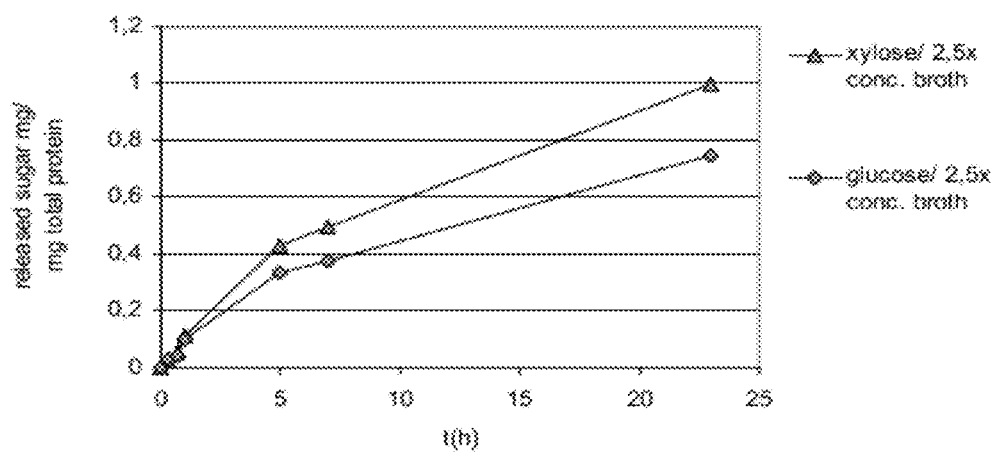
FIG. 18 Glucose released in the hydrolysis test per protein. As substrate was used 1 g cellulose. Some xylose was released from the hemicellulose originating from the culture broth used.

The sugar released during the hydrolysis tests as milligram per milliliter culture broth and milligram per milligram protein as a function of time is presented in FIGS. 12 to 15. FIG. 12 shows the xylose released in the hydrolysis test per volume of culture broth. As substrate was used 200 mg birch wood xylan. FIG. 13 shows the xylose released in the hydrolysis test per protein. As substrate was used 200 mg birch wood xylan. FIG. 14 shows the glucose released in hydrolysis tests per volume of culture broth. As substrate was used 1 g cellulose. Some xylose was released from the hemicellulose originating from the culture broth used. FIG. 15 shows the glucose released in the hydrolysis test per protein. As substrate was used 1 g cellulose. Some xylose was released from the hemicellulose originating from the culture broth used.

This example shows that *Aspergillus oryzae* can produce lipid and as a side product a culture broth with hydrolytic activities that can be re-used in the hydrolysis of lignocellulose material.

REFERENCES

Baer S H, Blaschek H P, Smith T L. 1987. Effect of Butanol Challenge and Temperature on Lipid Composition and Membrane Fluidity of Butanol-Tolerant *Clostridium acetobutylicum*. Applied and Environmental Microbiology 53: 2854-2861.

Fall R, Phelps P, Spindler D. 1984. Bioconversion of xylan to triglycerides by oil-rich yeasts. Applied and Environmental Microbiology. 47:1130-1134.

Lin H, Chang W, Ding H-T, Chen X-J, Zhou Q-F, Zhao Y-Hu. 2010. Direct microbial conversion of wheat straw into lipid by a cellulolytic fungus of *Aspergillus oryzae* A-4 in solid-state fermentation. Bioresource Technology 101:7556-7562.

Lynd L R, van Zyl W H, McBride J E, Laser M. 2005. Consolidated bioprocessing of cellulosic biomass: an update. Current Opinion in Biotechnology 16:577-583.

Suutari M, Liukkonen K, Laakso S. 1990. Temperature adaptation in yeasts: the role of fatty acids. Journal of General Microbiology 136: 1469-1474.

The invention claimed is:

1. An integrated process for single cell oil production and alcohol production, the process comprising steps:
   (a) cultivating a fungus belonging to the genus *Aspergillus* in a culture media in a single cell oil production process, wherein the culture media comprises hemicellulose and the fungus produces single cell oil and xylanase; and
   (b) cultivating a microorganism in a culture media in an alcohol production process, wherein the microorganism produces alcohol and the culture media comprises:
      (i) lignocellulosic material or fractions thereof, and the xylanase produced in step (a) or a fraction of the microorganism culture of step (a) that comprises the xylanase;
      or
      (ii) treated lignocellulosic material or fractions thereof; wherein the treated lignocellulosic material or fractions thereof have been treated with the xylanase produced in step (a), or wherein the treated lignocellulosic material or fractions thereof have been treated with a fraction of the microorganism culture of step (a) that comprises the xylanase.

2. The process according to claim 1, wherein the alcohol is ethanol, butanol, isopropanol, or mixtures thereof.

3. The process according to claim 1, further comprising separating a supernatant and the fungus cells from the culture of the single cell oil production process of step (a), and introducing the separated supernatant or the separated fungus cells to the culture media of the alcohol production process of step (b).

4. The process according to claim 1, further comprising separating a supernatant and the fungus cells from the culture of the single cell oil production process of step (a), treating lignocellulosic material or fractions thereof with the separated supernatant or the separated fungus cells, and introducing the treated lignocellulosic material or fractions thereof to the culture media of the alcohol production process of step (b).

5. The process according to claim 1, further comprising recovering the xylanase produced in the single cell oil production process of step (a) and introducing the recovered xylanase to the culture media of the alcohol production process of step (b).

6. The process according to claim 1, further comprising recovering the xylanase produced in the single cell oil production process of step (a), treating lignocellulosic material or fractions thereof with the recovered xylanase, and introducing the treated lignocellulosic material or fractions thereof to the culture media in the alcohol production process of step (b).

7. The process according to claim 1, wherein supernatant from the fungus culture of step (a) comprises the xylanase, and the culture media of step (b) comprises the supernatant, a dilution thereof, or a protein-enriched fraction thereof.

8. The process according to claim 1, further comprising recovering the single cell oil of the single cell oil production process of step (a) using a recovery method that preserves the catalytic activity of the xylanase produced in the single cell oil production process of step (a).

9. The process according to claim 1, wherein the culture media in the alcohol production process of step (b) further comprises starch.

10. The process according to claim 1, wherein the fungus in the single cell oil production process of step (a) further produces enzymes selected from the group consisting of hemicellulases, cellulases, mannanases, arabinases, galactosidases, glucosidases, mannosidases, xylosidases, arabinofuranosidase, esterases, endo-cellulases, exo-cellulases, cellobiases, beta-glucosidases, oxidative cellulases, cellulose phosphorylases and mixtures thereof.

11. The process according to claim 1, further comprising recovering the xylanase of the single cell oil production process of step (a), and recycling the recovered xylanase to culture media in a single cell oil production process.

12. The process according to claim 1, further comprising recovering lipids from the single cell oil production process of step (a) and reacting the lipids with alcohol in a transesterification reaction to produce biodiesel.

13. The process according to claim 1, further comprising recovering alcohol from the alcohol production process of step (b) and reacting the alcohol with lipids in a transesterification reaction to produce biodiesel.

* * * * *